(12) United States Patent
Pagi et al.

(10) Patent No.: US 11,730,420 B2
(45) Date of Patent: Aug. 22, 2023

(54) MATERNAL-FETAL SEPSIS INDICATOR

(71) Applicant: CERNER INNOVATION, INC., Kansas City, KS (US)

(72) Inventors: Prashant Pagi, Bengaluru (IN); Nishat Y., Bangalore (IN); Soumen Tapadar, Yelahanka (IN); Imran Shaikh, Bangalore (IN)

(73) Assignee: Cerner Innovation, Inc., Kansas City, MO (US)

( * ) Notice: Subject to any disclaimer, the term of this patent is extended or adjusted under 35 U.S.C. 154(b) by 520 days.

(21) Appl. No.: 16/717,299

(22) Filed: Dec. 17, 2019

(65) Prior Publication Data

US 2021/0177338 A1 Jun. 17, 2021

(51) Int. Cl.
  *A61B 5/00* (2006.01)
  *G16H 10/60* (2018.01)
(52) U.S. Cl.
  CPC ............ *A61B 5/412* (2013.01); *A61B 5/0011* (2013.01); *A61B 5/7275* (2013.01); *A61B 5/7435* (2013.01); *G16H 10/60* (2018.01)
(58) Field of Classification Search
  CPC combination set(s) only.
  See application file for complete search history.

(56) References Cited

U.S. PATENT DOCUMENTS

| | | |
|---|---|---|
| 4,839,853 A | 6/1989 | Deerwester et al. |
| 5,243,565 A | 9/1993 | Yamamoto |
| 5,301,109 A | 4/1994 | Landauer et al. |
| 5,664,109 A | 9/1997 | Johnson et al. |
| 5,809,494 A | 9/1998 | Nguyen |
| 5,835,900 A | 11/1998 | Fagg, III et al. |
| 6,039,688 A | 3/2000 | Douglas et al. |
| 6,122,628 A | 9/2000 | Castelli et al. |

(Continued)

FOREIGN PATENT DOCUMENTS

| | | |
|---|---|---|
| EP | 1043666 A2 | 10/2000 |
| EP | 2365456 A2 | 9/2011 |

(Continued)

OTHER PUBLICATIONS

Abbott et al., "Sequence Analysis and Optimal Matching Methods in Sociology, Review and Prospect", Sociological Methods & Research, vol. 29, Issue 1, Aug. 1, 2000, pp. 3-33.

(Continued)

*Primary Examiner* — Brian T Gedeon
*Assistant Examiner* — Joshua Andrew Schum-Houck
(74) *Attorney, Agent, or Firm* — Invoke

(57) ABSTRACT

Embodiments of the present disclosure describe methods, systems, and computer storage media for detecting sepsis in a maternal patient and causing for display a visual indicator of a graphical object. In some aspects sepsis may be detected based on a maternal patient's patient information and/or clinical diagnostic. Technologies described herein may be used to determine maternal-fetal sepsis and provide a graphical object of a patient's risk of the maternal-fetal sepsis. The visual indicator and graphical object may be identifiable to a clinician as a warning of a risk for maternal-fetal sepsis. In this way, maternal-fetal sepsis may be identified and a graphical object may be generated, facilitating timely treatment and early diagnosis of maternal-fetal sepsis.

30 Claims, 10 Drawing Sheets

(56) References Cited

U.S. PATENT DOCUMENTS

| | | |
|---|---|---|
| 6,246,964 B1 | 6/2001 | Blaunstein |
| 6,246,975 B1 | 6/2001 | Rivonelli et al. |
| 6,247,004 B1 | 6/2001 | Moukheibir |
| 6,397,224 B1 | 5/2002 | Zubeldia et al. |
| 6,618,715 B1 | 9/2003 | Johnson et al. |
| 6,654,740 B2 | 11/2003 | Tokuda et al. |
| 6,665,669 B2 | 12/2003 | Han et al. |
| 6,915,254 B1 | 7/2005 | Heinze et al. |
| 6,996,575 B2 | 2/2006 | Cox et al. |
| 7,039,634 B2 | 5/2006 | Xu et al. |
| 7,120,626 B2 | 10/2006 | Li et al. |
| 7,249,117 B2 | 7/2007 | Estes |
| 7,386,522 B1 | 6/2008 | Bigus et al. |
| 7,440,947 B2 | 10/2008 | Adcock et al. |
| 7,447,643 B1 | 11/2008 | Olson et al. |
| 7,496,561 B2 | 2/2009 | Caudill et al. |
| 7,529,765 B2 | 5/2009 | Brants et al. |
| 7,555,425 B2 | 6/2009 | Oon |
| 7,558,778 B2 | 7/2009 | Carus et al. |
| 7,617,078 B2 | 11/2009 | Rao et al. |
| 7,640,171 B2 | 12/2009 | Gendron et al. |
| 7,657,540 B1 | 2/2010 | Bayliss |
| 7,668,820 B2 | 2/2010 | Zuleba |
| 7,720,846 B1 | 5/2010 | Bayliss |
| 7,831,423 B2 | 11/2010 | Schubert |
| 7,844,449 B2 | 11/2010 | Lin et al. |
| 7,844,566 B2 | 11/2010 | Wnek |
| 7,853,456 B2 | 12/2010 | Soto et al. |
| 7,865,373 B2 | 1/2011 | Punzak et al. |
| 7,899,764 B2 | 3/2011 | Martin et al. |
| 7,899,796 B1 | 3/2011 | Borthwick et al. |
| 7,900,052 B2 | 3/2011 | Jonas |
| 7,912,842 B1 | 3/2011 | Bayliss |
| 7,933,909 B2 | 4/2011 | Trepetin |
| 7,953,685 B2 | 5/2011 | Liu et al. |
| 8,015,136 B1 | 9/2011 | Baker et al. |
| 8,078,554 B2 | 12/2011 | Fung et al. |
| 8,126,736 B2 | 2/2012 | Anderson et al. |
| 8,160,895 B2 | 4/2012 | Schmitt et al. |
| 8,165,893 B1 | 4/2012 | Goldberg et al. |
| 8,200,505 B2 | 6/2012 | Walker et al. |
| 8,515,777 B1 | 8/2013 | Rajasenan |
| 8,539,424 B2 | 9/2013 | Tetelbaum |
| 8,589,424 B1 | 11/2013 | Patel et al. |
| 8,666,785 B2 | 3/2014 | Baluta et al. |
| 8,838,628 B2 | 9/2014 | Leighton et al. |
| 8,856,156 B1 | 10/2014 | McNair et al. |
| 9,375,142 B2 | 6/2016 | Schultz et al. |
| 9,542,532 B1 | 1/2017 | McNair et al. |
| 9,542,647 B1 | 1/2017 | Mirhaji |
| 9,734,146 B1 | 8/2017 | McNair et al. |
| 10,198,499 B1 | 2/2019 | McNair et al. |
| 10,249,385 B1 | 4/2019 | McNair et al. |
| 10,268,687 B1 | 4/2019 | McNair et al. |
| 10,431,336 B1 | 10/2019 | Murrish et al. |
| 10,446,273 B1 | 10/2019 | McNair et al. |
| 10,483,003 B1 | 11/2019 | McNair et al. |
| 10,580,524 B1 | 3/2020 | McNair et al. |
| 10,628,553 B1 | 4/2020 | Murrish et al. |
| 10,769,241 B1 | 9/2020 | McNair |
| 10,854,334 B1 | 12/2020 | McNair et al. |
| 10,946,311 B1 | 3/2021 | McNair |
| 10,957,449 B1 | 3/2021 | McNair et al. |
| 11,100,933 B2 | 8/2021 | Lefkofsky et al. |
| 2002/0007284 A1 | 1/2002 | Schurenberg et al. |
| 2002/0023067 A1 | 2/2002 | Garland et al. |
| 2002/0032583 A1 | 3/2002 | Joao |
| 2002/0035486 A1 | 3/2002 | Huyn et al. |
| 2002/0038227 A1 | 3/2002 | Fey et al. |
| 2002/0038308 A1 | 3/2002 | Cappi |
| 2002/0042793 A1 | 4/2002 | Choi |
| 2002/0073138 A1 | 6/2002 | Gilbert et al. |
| 2002/0128860 A1 | 9/2002 | Leveque et al. |
| 2003/0023571 A1 | 1/2003 | Barnhill |
| 2003/0038308 A1 | 2/2003 | Kim |
| 2003/0055679 A1 | 3/2003 | Soil et al. |
| 2003/0163057 A1 | 8/2003 | Flick et al. |
| 2003/0212580 A1 | 11/2003 | Shen |
| 2004/0199332 A1 | 10/2004 | Iliff |
| 2004/0230105 A1 | 11/2004 | Geva et al. |
| 2004/0260666 A1 | 12/2004 | Pestotnik et al. |
| 2005/0027562 A1 | 2/2005 | Brown |
| 2005/0049497 A1 | 3/2005 | Krishnan et al. |
| 2005/0055246 A1 | 3/2005 | Simon |
| 2005/0119534 A1 | 6/2005 | Trost et al. |
| 2005/0144042 A1 | 6/2005 | Joffe et al. |
| 2005/0256740 A1 | 11/2005 | Kohan et al. |
| 2005/0272984 A1 | 12/2005 | Huiku |
| 2005/0288910 A1 | 12/2005 | Schlessinger et al. |
| 2006/0020465 A1 | 1/2006 | Cousineau et al. |
| 2006/0036619 A1 | 2/2006 | Fuerst et al. |
| 2006/0064447 A1 | 3/2006 | Malkov |
| 2006/0074824 A1 | 4/2006 | Li |
| 2006/0129427 A1 | 6/2006 | Wennberg |
| 2006/0161457 A1 | 7/2006 | Rapaport et al. |
| 2006/0173663 A1 | 8/2006 | Langheier et al. |
| 2006/0205564 A1 | 9/2006 | Peterson |
| 2006/0206027 A1 | 9/2006 | Malone |
| 2006/0206359 A1 | 9/2006 | Stang |
| 2006/0218010 A1 | 9/2006 | Michon et al. |
| 2006/0271556 A1 | 11/2006 | Mukherjee et al. |
| 2007/0005621 A1 | 1/2007 | Lesh et al. |
| 2007/0026365 A1 | 2/2007 | Friedrich et al. |
| 2007/0031873 A1 | 2/2007 | Wang et al. |
| 2007/0094048 A1 | 4/2007 | Grichnik |
| 2007/0106533 A1 | 5/2007 | Greene |
| 2007/0106752 A1 | 5/2007 | Moore |
| 2007/0233391 A1 | 10/2007 | Milstein et al. |
| 2007/0239482 A1 | 10/2007 | Finn et al. |
| 2007/0244724 A1 | 10/2007 | Pendergast et al. |
| 2008/0021288 A1 | 1/2008 | Bowman et al. |
| 2008/0046292 A1 | 2/2008 | Myers et al. |
| 2008/0091088 A1* | 4/2008 | Kiani .............. A61M 5/1723 600/301 |
| 2008/0097938 A1 | 4/2008 | Guyon et al. |
| 2008/0131374 A1 | 6/2008 | Medich et al. |
| 2008/0133269 A1 | 6/2008 | Ching |
| 2008/0147438 A1 | 6/2008 | Kil |
| 2008/0147441 A1 | 6/2008 | Kil |
| 2008/0172214 A1 | 7/2008 | Col et al. |
| 2008/0172251 A1 | 7/2008 | Reichert et al. |
| 2008/0183454 A1 | 7/2008 | Barabasi et al. |
| 2008/0195422 A1 | 8/2008 | Nessinger et al. |
| 2008/0243548 A1 | 10/2008 | Cater |
| 2008/0249376 A1 | 10/2008 | Zaleski |
| 2008/0255884 A1 | 10/2008 | Carus et al. |
| 2008/0256006 A1 | 10/2008 | Buscema et al. |
| 2008/0268413 A1 | 10/2008 | Leichner |
| 2008/0275731 A1 | 11/2008 | Rao et al. |
| 2008/0287746 A1 | 11/2008 | Reisman |
| 2008/0288292 A1 | 11/2008 | Bi et al. |
| 2008/0288474 A1 | 11/2008 | Chin et al. |
| 2008/0294692 A1 | 11/2008 | Angell et al. |
| 2008/0301177 A1 | 12/2008 | Doherty |
| 2008/0306926 A1 | 12/2008 | Friedlander et al. |
| 2009/0006431 A1 | 1/2009 | Agrawal et al. |
| 2009/0012928 A1 | 1/2009 | Lussier et al. |
| 2009/0112892 A1 | 4/2009 | Cardie et al. |
| 2009/0125333 A1 | 5/2009 | Heywood et al. |
| 2009/0132284 A1 | 5/2009 | Fey et al. |
| 2009/0164249 A1 | 6/2009 | Hunt et al. |
| 2009/0228303 A1 | 9/2009 | Faulkner et al. |
| 2009/0259493 A1 | 10/2009 | Venon et al. |
| 2009/0299767 A1 | 12/2009 | Michon et al. |
| 2009/0299977 A1 | 12/2009 | Rosales |
| 2009/0304246 A1 | 12/2009 | Walker et al. |
| 2009/0313041 A1 | 12/2009 | Eder |
| 2009/0318775 A1 | 12/2009 | Michelson et al. |
| 2009/0319295 A1 | 12/2009 | Kass-Hout et al. |
| 2010/0082369 A1 | 4/2010 | Prenelus et al. |
| 2010/0088117 A1 | 4/2010 | Belden et al. |
| 2010/0121883 A1 | 5/2010 | Cutting et al. |
| 2010/0131434 A1 | 5/2010 | Magent et al. |
| 2010/0131438 A1 | 5/2010 | Pandya et al. |

(56) References Cited

U.S. PATENT DOCUMENTS

| | | |
|---|---|---|
| 2010/0131482 A1 | 5/2010 | Linthicum et al. |
| 2010/0131883 A1 | 5/2010 | Linthicum et al. |
| 2010/0142774 A1 | 6/2010 | Ben-Haim et al. |
| 2010/0145720 A1 | 6/2010 | Reiner |
| 2010/0153133 A1 | 6/2010 | Angell et al. |
| 2010/0179818 A1 | 7/2010 | Kelly et al. |
| 2010/0185685 A1 | 7/2010 | Chew et al. |
| 2010/0198755 A1 | 8/2010 | Soll et al. |
| 2010/0235330 A1 | 9/2010 | Reiner |
| 2010/0274576 A1 | 10/2010 | Young |
| 2010/0293003 A1 | 11/2010 | Abbo |
| 2010/0299155 A1 | 11/2010 | Findlay et al. |
| 2010/0324861 A1 | 12/2010 | Goulding et al. |
| 2010/0324938 A1 | 12/2010 | Ennett et al. |
| 2011/0010401 A1 | 1/2011 | Adams et al. |
| 2011/0015937 A1 | 1/2011 | Janas, III et al. |
| 2011/0046979 A1 | 2/2011 | Tulipano et al. |
| 2011/0067108 A1 | 3/2011 | Hoglund |
| 2011/0077973 A1 | 3/2011 | Breitenstein et al. |
| 2011/0087501 A1 | 4/2011 | Severin |
| 2011/0093467 A1 | 4/2011 | Sharp et al. |
| 2011/0119089 A1 | 5/2011 | Carlisle |
| 2011/0161110 A1 | 6/2011 | Mault |
| 2011/0201900 A1 | 8/2011 | Zhang et al. |
| 2011/0225001 A1 | 9/2011 | Shen |
| 2011/0246238 A1 | 10/2011 | Vdovjak et al. |
| 2011/0270629 A1 | 11/2011 | Abbo |
| 2011/0295621 A1 | 12/2011 | Farooq et al. |
| 2011/0306845 A1 | 12/2011 | Osorio |
| 2012/0016685 A1 | 1/2012 | Ryan et al. |
| 2012/0020536 A1 | 1/2012 | Moehrle |
| 2012/0047105 A1 | 2/2012 | Saigal et al. |
| 2012/0059779 A1 | 3/2012 | Syed et al. |
| 2012/0072235 A1 | 3/2012 | Varadarajan et al. |
| 2012/0078127 A1 | 3/2012 | McDonald et al. |
| 2012/0086963 A1 | 4/2012 | Fujitsuka et al. |
| 2012/0089420 A1 | 4/2012 | Hoffman et al. |
| 2012/0089421 A1* | 4/2012 | Hoffman ............... G16H 50/30 705/3 |
| 2012/0095780 A1 | 4/2012 | McNair |
| 2012/0109685 A1 | 5/2012 | Carter et al. |
| 2012/0110016 A1 | 5/2012 | Phillips |
| 2012/0173475 A1 | 7/2012 | Ash et al. |
| 2012/0174014 A1 | 7/2012 | Ash et al. |
| 2012/0174018 A1 | 7/2012 | Ash et al. |
| 2012/0175475 A1 | 7/2012 | McErlane |
| 2012/0185275 A1 | 7/2012 | Loghmani |
| 2012/0203575 A1 | 8/2012 | Tulipano et al. |
| 2012/0215784 A1 | 8/2012 | King et al. |
| 2012/0232930 A1 | 9/2012 | Schmidt et al. |
| 2012/0246102 A1 | 9/2012 | Sudharsan |
| 2013/0006911 A1 | 1/2013 | Christie, IV et al. |
| 2013/0023434 A1 | 1/2013 | Van Laar |
| 2013/0031613 A1 | 1/2013 | Shanabrook et al. |
| 2013/0046529 A1 | 2/2013 | Grain et al. |
| 2013/0046558 A1 | 2/2013 | Landi et al. |
| 2013/0073311 A1* | 3/2013 | Lynn ..................... G16H 50/20 705/2 |
| 2013/0110547 A1 | 5/2013 | Englund et al. |
| 2013/0110548 A1 | 5/2013 | Kutty |
| 2013/0132308 A1 | 5/2013 | Boss et al. |
| 2013/0132312 A1 | 5/2013 | Lee et al. |
| 2013/0132323 A1 | 5/2013 | Soto et al. |
| 2013/0158968 A1* | 6/2013 | Ash ...................... G16H 50/20 703/11 |
| 2013/0197938 A1 | 8/2013 | Bayouk et al. |
| 2013/0245389 A1 | 9/2013 | Schultz et al. |
| 2014/0081652 A1 | 3/2014 | Klindworth |
| 2014/0095184 A1 | 4/2014 | Gotz et al. |
| 2014/0095186 A1 | 4/2014 | Gotz et al. |
| 2014/0180699 A1 | 6/2014 | Massa et al. |
| 2014/0181128 A1 | 6/2014 | Riskin et al. |
| 2014/0200414 A1 | 7/2014 | Osorio |
| 2014/0336539 A1 | 11/2014 | Torres et al. |
| 2015/0049947 A1 | 2/2015 | Katsaros et al. |
| 2015/0161329 A1 | 6/2015 | Mabotuwana et al. |
| 2015/0193583 A1 | 7/2015 | McNair et al. |
| 2015/0254408 A1 | 9/2015 | Mahtani et al. |
| 2015/0324535 A1 | 11/2015 | Ash et al. |
| 2015/0363559 A1 | 12/2015 | Jackson et al. |
| 2016/0004840 A1 | 1/2016 | Rust et al. |
| 2016/0063212 A1 | 3/2016 | Monier et al. |
| 2016/0143594 A1 | 5/2016 | Moorman et al. |
| 2017/0098358 A1* | 4/2017 | Bechtel ................. G16H 20/60 |
| 2017/0124269 A1 | 5/2017 | McNair et al. |
| 2019/0336085 A1* | 11/2019 | Kayser .................. A61B 5/447 |
| 2020/0043612 A1 | 2/2020 | McNair et al. |
| 2020/0335179 A1 | 10/2020 | Stojadinovic et al. |

FOREIGN PATENT DOCUMENTS

| | | |
|---|---|---|
| WO | 2006/002465 A1 | 1/2006 |
| WO | 2009/112977 A1 | 9/2009 |
| WO | 2012/122122 A1 | 9/2012 |
| WO | 2012/122195 A1 | 9/2012 |
| WO | 2012/122196 A2 | 9/2012 |

OTHER PUBLICATIONS

Agrawal et al., "Fast Discovery of Association Rules", Advances in Knowledge Discovery and Data Mining, Feb. 1996, pp. 307-328.

Aronson, Alan R., "MetaMap: Mapping Text to the UMLS Metathesaurus", Jul. 14, 2006, pp. 1-26.

Arpaia et al. "Multi-Agent Remote Predictive Diagnosis of Dangerous Good Transports", Instrumentation and Measurement Technology Conference Proceedings, vol. 3, May 16-19, 2005, pp. 1685-1690.

Berchtold et al., "The Mixture Transition Distribution Model for High-Order Markov Chains and Non-Gaussian Time Series", Statistical Science, vol. 17, No. 3, 2002, pp. 328-356.

Berry et al., "Care Coordination for Patients With Complex Health Profiles in Inpatients and Outpatient Settings", Mayo Clinic Proceedings, vol. 88, No. 2, Feb. 2013, pp. 184-194.

Billari et al., "Timing, Sequencing, and quantum of Life Course Events: A Machine-Learning Approach", European Journal of Population, vol. 22, Mar. 2006, pp. 37-65.

Cohen et al., "Integrated Complex Care Coordination For Children With Medical Complexity: A Mixed-Methods Evaluation Of Tertiary Care-Community Collaboration", BMC Health Services Research, vol. 12, Oct. 23, 2012, pp. 1-11.

Deville et al., "Correspondence Analysis with an Extension Towards Nominal Time Series", Journal of Econometrics, vol. 22, 1983, pp. 169-189.

Dijkstra et al., "Measuring the Agreement Between Sequences", Sociological Methods & Research, vol. 24, Issue 2, Nov. 1, 1995, pp. 214-231.

Dvorak et al., "Football Injuries and Physical Symptoms: A Review of the Literature", American Journal of Sports Medicine, vol. 28, Issue 5_suppl, Sep. 1, 2000, pp. S3-S9.

Dvorak et al., "Risk Factor Analysis for Injuries in Football Players:Possibilities for a Prevention Program", American Journal of Sports Medicine, vol. 28, Issue 5_suppl, Sep. 1, 2000, pp. S69-S74.

Han et al., "Frequent Pattern Mining: Current Status and Future Directions", Data Mining and Knowledge Discovery, vol. 15, Jan. 27, 2007, pp. 55-86.

Hawkins et al., "A Prospective Epidemiological Study of Injuries in Four English Professional Football Clubs", British Journal of Sports Medicine, vol. 33, 1999, pp. 196-203.

Huyse et al., "COMPRI—An Instrument to Detect Patients With Complex Care Needs: Results from a European Study", Psychosomatics, vol. 42, No. 3, May-Jun. 2001, pp. 222-228.

Junge et al., "Soccer Injuries: A Review on Incidence and Prevention", Sports Medicine, vol. 34, No. 13, 2004, pp. 929-938.

Kang et al., "Mining Based Decision Support Multi-agent System for Personalized e-Healthcare Service", Proceedings of the 2nd KES International conference on Agent and Multi-Agent Systems: Technologies and Applications, Mar. 2008, pp. 733-742.

(56) References Cited

OTHER PUBLICATIONS

Kiran et al., "An Improved Multiple Minimum Support Based Approach to Mine Rare Association Rules", IEEE Symposium on Computational Intelligence and Data Mining, 2009, pp. 340-347.
Mabry et al., "Clinical Decision Support with IM-Agents and ERMA Multi-agents", Proceedings of the 17th IEEE Symposium on Computer-Based Medical Systems, Jun. 2004, 6 pages.
Nealon et al., "Agent-Based Applications in Health Care", Applications of Software Agent Technology in the Health Dare Domain, 2003, pp. 3-18.
Nielsen et al., "Epidemiology and Traumatology of Injuries in Soccer", The American Journal of Sports Medicine, vol. 17, No. 6, Nov. 1, 1989, pp. 803-807.
Ohno-Machado, Lucila, "Realizing the Full Potential of Electronic Health Records: The Role of Natural Language Processing", Journal of American Medical Information Association, vol. 18, No. 5, Sep. 2011, p. 539.
Roever, Christian, "Package 'Bayesian Spectral Inference'", Available online at: <r-project.org>, Apr. 30, 2015, pp. 1-29.
Sariyar et al., "The RecordLinkage Package: Detecting Errors in Data", The R Journal, vol. 2, No. 2, Dec. 2010, pp. 61-67.
Zaki, Mohammed J., "SPADE: An Efficient Algorithm for Mining Frequent Sequences", Machine Learning, vol. 42, Jan. 2001, pp. 31-60.
Final Office Action received for U.S. Appl. No. 14/555,058, dated Feb. 12, 2020, 22 pages.
First Action Interview Office Action received for U.S. Appl. No. 15/386,876, dated Jan. 28, 2020, 24 pages.
Non-Final Office Action received for U.S. Appl. No. 13/269,244, dated Apr. 8, 2020, 17 pages.
Notice of Allowance received for U.S. Appl. No. 16/588,647, dated Apr. 1, 2021, 21 pages.
Notice of Allowance received for U.S. Appl. No. 14/982,982, dated Sep. 13, 2021, 15 pages.
Pre-Interview First Office action received for U.S. Appl. No. 17/011,474, dated Sep. 28, 2021, 5 pages.
John et al., "Neuro-Fuzzy Clustering Of Radiographic Tibia Image Data Using Type 2 Fuzzy Sets", Information Sciences, vol. 125, Issues 1-4, 2000, ISSN 0020-0255, Available on Internet at: <https://www.sciencedirect.com/science/article/pii/S0020025500000009>, 2000, pp. 65-82.
Final Office Action received for U.S. Appl. No. 14/148,039, dated Feb. 1, 2021, 17 pages.
Final Office Action received for U.S. Appl. No. 15/386,876, dated Jan. 11, 2021, 16 pages.
Non-Final Office Action received for U.S. Appl. No. 16/868,642, dated Feb. 4, 2021, 24 pages.
Summons to Attend Oral Proceedings received for European Patent Application No. 14835964.9, mailed on Jan. 13, 2021, 12 pages.
Abernethy et al., "Eliciting Consumer Preferences Using Robust Adaptive Choice Questionnaires", IEEE Transactions on Knowledge and Data Engineering, vol. 20, No. 2, Feb. 2008, pp. 145-155.
Othman et al., "Agent Based Preprocessing", International Conference on Intelligent and Advanced Systems 2007, 2007, pp. 219-223.
Ta et al., "Data Descriptor: Columbia Open Health Data, Clinical Concept Prevalence and Co-occurrence from Electronic Health Records", Scientific data, vol. 5,180273, doi: 10.1038/sdata.2018.273, Nov. 27, 2018, pp. 1-17.
Uhrmacher et al., "Distributed, Parallel Simulation of Multiple, Deliberative Agents", Proceedings of the fourteenth workshop on Parallel and distributed simulation. May 2000, pp. 101-108.
Notice of Allowance received for U.S. Appl. No. 13/269,244, dated Dec. 14, 2021, 9 pages.
Pre-Interview First Office Action received for U.S. Appl. No. 16/714,221, dated Jan. 27, 2022, 5 pages.
Seibig et al., "Collection of Annotated Data in a Clinical Validation Study for Alarm Algorithms in Intensive Care—A Methodologic Framework", Journal of Critical Care, vol. 25, 2010, pp. 128-135.
Notice of Allowance received for U.S. Appl. No. 16/793,870, dated Feb. 8, 2022, 18 pages.
Non-Final Office Action received for U.S. Appl. No. 16/819,890, dated Sep. 29, 2020, 12 pages.
Non-Final Office Action received for U.S. Appl. No. 15/386,876, dated Sep. 14, 2020, 15 pages.
Notice of Allowance received for U.S. Appl. No. 14/148,046, dated Oct. 7, 2020, 11 pages.
The Comprehensive R Archive Network, R, Available online at: <http://cran.r-project.org>, Retrieved on Feb. 27, 2020, 1 page.
Cook et al., "Making Prophecies with Decision Predicates", ACM 978-1-4503-0490-0/11/01, Jan. 2011, 14 pages.
Prados-Suarez et al., "Contextualized Access to Electronical Health Records in Cardiology", IEEE Transactions on Information Technology in Biomedicine, vol. 16, No. 3, doi: 10.1109/TITB.2011.2178033., May 2012, pp. 401-412.
Final Office Action received for U.S. Appl. No. 14/209,568, dated Jul. 12, 2021, 9 pages.
Final Office action received for U.S. Appl. No. 14/555,058, dated Jun. 22, 2021, 12 pages.
Non-Final Office action received for U.S. Appl. No. 16/237,304, dated Jul. 7, 2021, 13 pages.
Non-Final Office Action received for U.S. Appl. No. 16/819,890, dated Jun. 24, 2021, 14 pages.
Notice of Allowance received for U.S. Appl. No. 15/855,720, dated Jun. 1, 2021, 15 pages.
Preinterview First Office Action received for U.S. Appl. No. 16/601,311, dated Jun. 15, 2021, 4 pages.
Duff, Si., "Development and history of sparse direct methods", SIAM Conference on Applied Linear Algebra, Available online at: <http://www,numerical.rl.ac.uk/people/isd/isd,html>, Oct. 26-29, 2009, 44 pages.
Shirabad et al., "Implementing an Integrative Multi-agent Clinical Decision Support System with Open Source Software", Journal of Medical Systems 36, Available online at: <https://doi.org/10.1007/s10916-010-9452-9>, 2012, pp. 123-137.
Xue et al., "Fast Query by Example of Environmental Sounds via Robust and Efficient Cluster-based Indexing", 2008 IEEE, International Conference on Acoustics, Speech and Signal Processing, Available online at: <doi: 10.1109/ICASSP.2008.4517532>, 2008, pp. 5-8.
Final Office Action received for U.S. Appl. No. 13/269,244, dated Aug. 12, 2020, 18 pages.
Final Office Action received for U.S. Appl. No. 14/148,059, dated Jul. 16, 2020, 16 pages.
Final Office Action received for U.S. Appl. No. 15/855,720, dated Jul. 2, 2020, 15 pages.
Notice of Allowance received for U.S. Appl. No. 14/148,020, dated Jul. 22, 2020, 10 pages.
Appavoo et al., "Enabling Autonomic Behavior in Systems Software With Hot Swapping", IBM Systems Journal, vol. 42, No. 1, 2003, pp. 60-76.
Townsend, Hilary, "Natural Language Processing and Clinical Outcomes: The Promise and Progress of NLP for Improved Care", Journal of AHIMA, vol. 84, No. 2, Available online at: <https://bok.ahima.org/doc?oid=106198#.X0SgnSgzY2x>, Mar. 2013, 3 pages.
Notice of Allowance received for U.S. Appl. No. 14/148,039, dated Jul. 11, 2020, 10 pages.
First Action Interview Office Action received for U.S. Appl. No. 16/714,221, dated Apr. 4, 2022, 19 pages.
Non-Final Office Action received for U.S. Appl. No. 16/819,890, dated Apr. 28, 2022, 17 pages.
Final Office Action received for U.S. Appl. No. 16/819,890, dated Oct. 27, 2022, 17 pages.
Final Office Action received for U.S. Appl. No. 17/011,474, dated Oct. 12, 2022, 17 pages.
Notice of Allowance received for U.S. Appl. No. 17/387,786, dated Nov. 30, 2022, 16 pages.

\* cited by examiner

ADD PREGNANCY

ACTIVE PREGNANCY HAS BEEN FOUND.

PREGNANCY OVERVIEW

408 — 410 — CANCEL PREGNANCY   CLOSE PREGNANCY   MODIFY PREGNANCY

CURRENT PREGNANCY | CONTACT INFORMATION

| EDD | 07/17/19 |
| EGA | (AUTHORITATIVE) 39 WEEKS, 6 DAYS |
| GRAVIDA/PARITY | G1,P0(0,0,0,0) |
| MULTIPLE FETUSES | NO |
| FEEDING PLAN | -- |
| SEPSIS | |

CURRENT WEIGHT --
PRE-PREG WEIGHT --
HEIGHT --
BMI --

BLOOD TYPE --

406

ADD PREGNANCY
PREGNANCY OVERVIEW
END VISIT
CHECKOUT
ADMIT TO INPATIENT 400
402
404

*FIG. 4.*

PRENATAL LABS & TESTS 12

⚑ RESULTS FOR INDICATED LAB FALL OUTSIDE OF THE RECOMMENDED GESTATIONAL AGE RANGE AND MAY BE SELECTED TO FULFILL THIS RANGE.

SEPSIS

| TEST NAME | RESULT | RESULT DATE | GESTATIONAL AGE |
|---|---|---|---|
| ▲ INITIAL LABS | | | |
| WEIGHT ESTIMATED | 57 KG | JUL 10, 2019 | 34W 5D |
| CERVIX DILATION | 33 CM | JUL 10, 2019 | 34W 5D |
| ▲ GROUP 1 | | | |
| CERVIX EFFACEMENT | ⚑ | -- | -- |
| SYSTOLIC BLOOD PRESSURE | ⚑ | -- | -- |
| ▲ TRANSCRIBED | | | |
| SYSTOLIC BLOOD PRESSURE | ⚑ | -- | -- |
| ▲ TRANSCRIBED LABS | | | |

PREGNANCY OVERVIEW
RESULTS TIMELINE
PRENATAL LAB & TESTS 12

*FIG. 5.*

MATERNAL-FETAL SEPSIS INDICATOR

BACKGROUND

The development of sepsis has been considered an underlying cause of 11% of maternal deaths, according to some studies. Sepsis is a significant contributor to fetal mortality and is attributed to other underlying conditions. Sepsis can result from an infection anywhere in the body in the presence of an infection with a Systemic Inflammatory Response Syndrome (SIRS) response. For example, sepsis can result from pneumonia, influenza, or urinary tract infections. When sepsis is diagnosed in a patient during pregnancy, or during labor the condition is referred to as "maternal-fetal sepsis", indicating the condition of sepsis in the mother and the fetus. Maternal-fetal sepsis can be deadly to both the mother and the fetus. When a maternal patient (e.g., a mother) is affected by sepsis the same condition may be transferred to the fetus. Maternal-fetal sepsis can be life changing even to survivors, causing chronic pain, fatigue, organ dysfunction, and post-traumatic stress disorder. Early diagnosis and timely treatment can increase the likelihood of survival of maternal-fetal sepsis for the mother and/or fetus.

On account of these clinical risks, it is of considerable value to have the improved technologies, as described in the present disclosure, of detecting maternal-fetal sepsis and causing for display a visual indicator of a graphical object. Detecting maternal-fetal sepsis and generating a graphical object, as described in the improved technologies of the present disclosure, can help with timely treatment and early diagnosis.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In brief and at a high level, this disclosure describes, among other things, methods, systems, and computer storage media for detecting maternal-fetal sepsis and causing for display a visual indicator of a graphical object (e.g., a notification). Technologies described herein may be utilized to determine maternal-fetal sepsis from received patient information. In particular, technologies describe, in some aspects, displaying a maternal-fetal sepsis indicator when a sepsis condition is detected during pregnancy, or during labor. Technologies may be used to determine maternal-fetal sepsis and provide a graphical object of a patient's risk of the maternal-fetal sepsis. Improved notification is provided when a patient is determined to have the maternal-fetal sepsis condition. Some aspects cause for display a graphical object to indicate the presence of maternal-fetal sepsis condition to the mother and/or fetus. For example, on a graphical user interface (GUI) a first visual indicator of a graphical object in response to determining an actionable sepsis criteria and a risk assessment array have been satisfied. In some aspects, a second visual indicator of a graphical object may be displayed on the GUI in response to a first indication that a maternal patient and fetus are at risk of maternal-fetal sepsis. The risk of maternal-fetal sepsis defining at least a likelihood of being diagnosed with sepsis. The second visual indicator may be changed to a first visual indicator of the graphical object in response to a second indication based on a clinical diagnostic for the maternal patient. The visual indicator and graphical object may be identifiable to a clinician as a warning of a risk for maternal-fetal sepsis. In this way, maternal-fetal sepsis may be identified and a graphical object may be generated, facilitating timely treatment and early diagnosis of maternal-fetal sepsis.

BRIEF DESCRIPTION OF THE DRAWINGS

The present invention is described in detail below and with reference to the attached drawing figures, wherein:

FIGS. 3A-3B and 4-5 are an exemplary screen display of a visual indicator of a graphical object for maternal-fetal sepsis, in accordance with aspects of the present invention;

DETAILED DESCRIPTION OF THE INVENTION

Figure 1A:
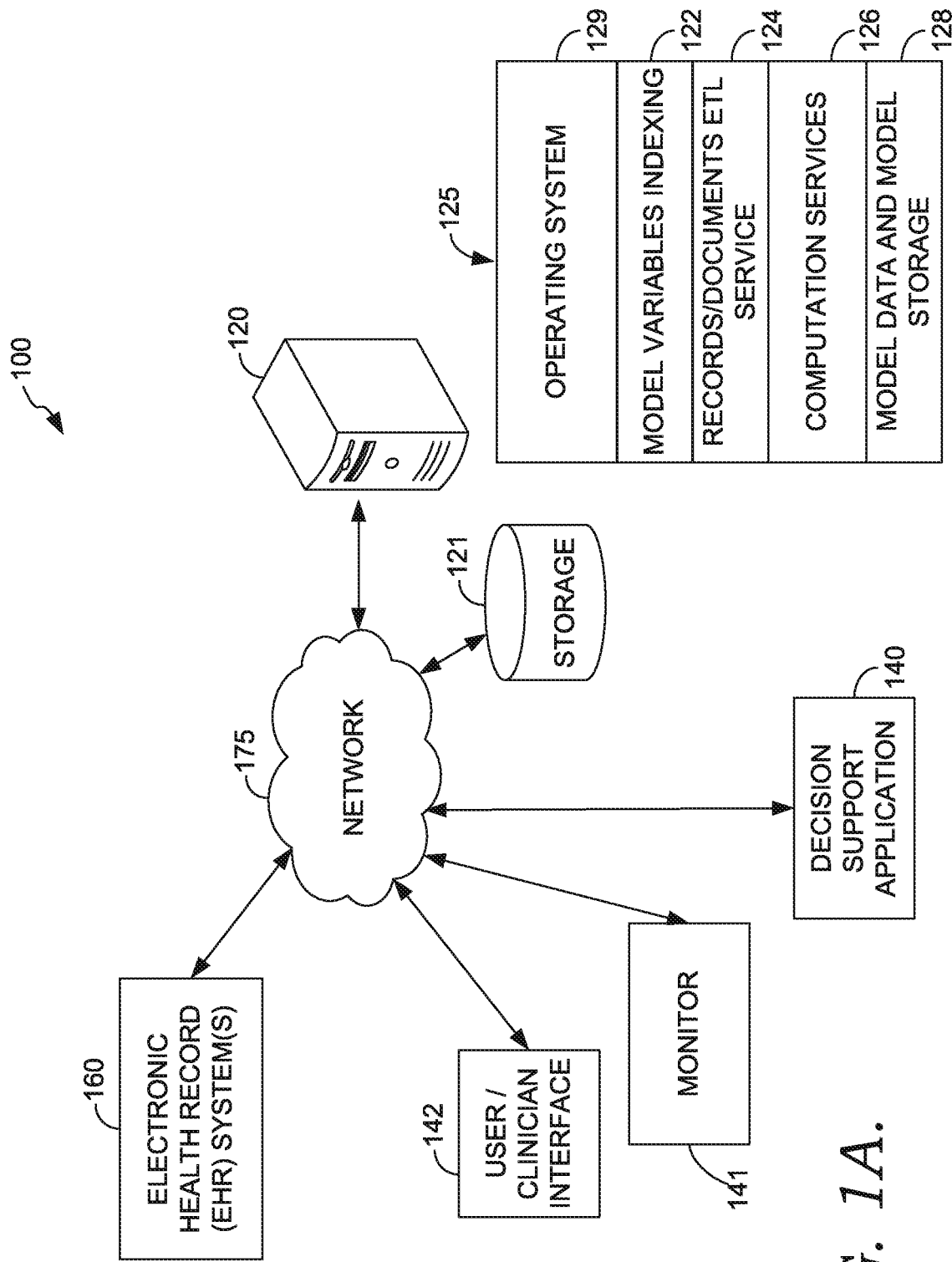
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, aspects of the invention may be embodied as, among other things: a method, system, or set of instructions embodied on one or more computer-readable media. Accordingly, the aspects may take the form of a hardware embodiment, a software embodiment, or an embodiment combining software and hardware. In one embodiment, the invention takes the form of a computer-program product that includes computer-usable instructions embodied on one or more computer-readable media, as discussed further with respect to FIGS. 1A-1B.

At a high level, this disclosure describes, among other things, methods, systems, and computer storage media for detecting maternal-fetal sepsis and causing for display a notification. In exemplary aspects, the visual indicator of a graphical object is caused for display in response to determining an actionable sepsis-specific criteria and the risk assessment array have been satisfied. The risk assessment array may be a patient's risk of maternal-fetal sepsis based on maternal patient information, for example, a higher temperature, elevated heart rate, and/or an elevated white blood cell count. The risk of maternal-fetal sepsis may be described with regard to the risk assessment array, defining a patient has at least a likelihood of being diagnosed with maternal-fetal sepsis. The risk assessment array may represent the presence of organisms associated with sepsis in the patient. If both the actionable sepsis-specific criteria and the risk assessment array are satisfied, a first visual indicator of a graphical object may be presented. In some aspects, the methods and systems may be implemented as a decision support computer application or tool for detecting maternal-fetal sepsis and causing for display a visual indicator of a graphical object. For example, when a risk of maternal-fetal sepsis is determined by the methods described herein, a visual indicator of a graphical object may be generated.

As previously explained, maternal-fetal sepsis has many health risks for any patient. Maternal-fetal sepsis can show similar symptoms pregnant patients. Maternal-fetal sepsis can be identified by higher than normal temperatures, elevated heart rate, and/or an elevated white blood cell count, but each of these items can be normal for pregnancy. If maternal-fetal sepsis is successfully identified in these cases, the condition can be overcome with timely treatment. However, studies have shown that 20 percent of mothers who did not receive antibiotics within the first hour of the onset of maternal-fetal sepsis have died along with their fetus, and those who survive end up with either an abortion or premature deliveries. Time is of the essence to identify and treat this condition.

To combat the problems with identifying maternal-fetal sepsis, it is important to notify a clinician of the risk of maternal-fetal sepsis. However, it is difficult to determine maternal-fetal sepsis based on one single test. Many factors relating to a patient's current condition and medical history may contribute to determining the patient is at risk of maternal-fetal sepsis. No tools exist for alerting a clinician of a patient's risk of maternal-fetal sepsis. Instead of a tool, a clinician may have to identify maternal-fetal sepsis using any information available from desperate systems. Further, a clinician may have to identify maternal-fetal sepsis using outdated information from the desperate systems. Without this information, clinicians often do not treat maternal-fetal sepsis until it is too late for the patient and/or the fetus. There exists a need to determine a patient's risk of maternal-fetal sepsis and provide a visual indicator of an object to notify a clinician of the patient's risk of maternal-fetal sepsis.

Accordingly, aspects of the present disclosure aim to determine a risk of maternal-fetal sepsis and cause for display on a graphical user interface a visual indicator of a graphical object (e.g., a notification). This process may include determining a patient has satisfied a risk assessment array or an actionable-sepsis-specific criteria has been satisfied. The identification of this risk of maternal-fetal sepsis can be beneficial to clinicians, who may recommend additional testing in response to the identified risk. In some aspects, the process may include changing a second visual indicator to a first visual indicator of the graphical object in response to satisfying the sepsis-specific criteria. The visual indicator of the graphical object or the change of the visual indicator can signal to a clinician the risk level of a patient and treat the patient accordingly. In some embodiments, the present invention also presents remedial actions to be performed by the patient.

Stated differently, aspects of the present disclosure are an improvement over prior art systems because they help identify a risk of maternal-fetal sepsis, determine actionable sepsis-specific criteria, and generate a notification for a clinician. With the present disclosure, a clinician can more quickly identify maternal-fetal sepsis and provide treatment, as described herein.

Specifically, aspects include receiving maternal patient information. This maternal patient information may correspond to a patient and may be from a source. In some aspects, maternal patient information may be from the patient's electronic medical record (EMR). In some aspects, the source may be an information system from a single medical organization or from a plurality of medical organizations. Based on the maternal patient information, a risk assessment array may be generated for the patient representing the patient's risk of maternal-fetal sepsis. For example, the risk assessment array may be based on the vitals of the patient. In some aspects, it may be determined the patient has satisfied the risk assessment array. A clinical diagnostic may be received for the patient representing the presence of organisms associated with maternal-fetal sepsis. An actionable sepsis-specific criteria may be determined to be satisfied based on the clinical diagnostic. In response to the determination the actionable sepsis-specific criteria and the risk assessment array have been satisfied, a first visual indicator of a graphical object may be caused for display on a GUI.

In another embodiment, indications may be received and a visual indicator may be generated according to the indication. Accordingly, a first indication that a maternal patient has satisfied a risk assessment array for the maternal patient's risk of maternal-fetal sepsis may be received. In response to the first indication, a second visual indicator of a graphical object may be caused for display on the GUI. A second indication may be received indicating an actionable sepsis-specific criteria has been met based on the clinical diagnostic for the maternal patient representing a presence of organisms associated with maternal-fetal sepsis in the maternal patient. The second visual indicator may be caused to change on the GUI in response to receiving the second indication. The second visual indicator may be caused to change to a first visual indicator of the graphical object. In some aspects, the second visual indicator caused to change to a first visual indicator may indicating receipt of the clinical diagnostic, for example the confirmation for presence of sepsis indicating organisms in the blood stream As used throughout this disclosure, the term "graphical object" may be any item to notify a clinician of a risk of maternal-fetal sepsis. A graphical object may be an item, symbol, image, figure, pattern, word, phrase, or icon. In some aspects, a graphical object may be a pictorial representation of maternal-fetal sepsis and/or a phrase.

Throughout this document, the term "visual indicator" may be used to refer to the means of display of the graphical object. A visual indicator may display the graphical object with a size, shape, color, position or other characteristic of visual display.

Although the invention may be described with regard to maternal-fetal sepsis, it is contemplated that the present invention may only be applicable to detection of sepsis during pregnancy. As described, maternal-fetal sepsis is a dangerous condition which requires quick treatment to increase the odds of survival. Embodiments of the present invention may be identifiable to a clinician as a warning of a risk for maternal-fetal sepsis during pregnancy. In this way, maternal-fetal sepsis may be identified and a graphical object may be generated, facilitating timely treatment and early diagnosis of maternal-fetal sepsis in any patient, d, as described herein.

Referring now to the drawings generally, and more specifically, referring to FIG. 1A, an aspect of an operating environment 100 is provided suitable for practicing an embodiment of this disclosure. Certain items in block-diagram form are shown more for being able to reference something consistent with the nature of a patent than to imply a certain component is or is not part of a certain device. Similarly, although some items are depicted in the singular form, plural items are contemplated as well (e.g., what is shown as one data store might really be multiple data stores distributed across multiple locations). But showing every variation of each item might obscure aspects of the invention. Thus, for readability, items are shown and referenced in the singular (while fully contemplating, where applicable, the plural).

As shown in FIG. 1A, example operating environment 100 provides an aspect of a computerized system for detecting maternal-fetal sepsis and causing for display a visual indicator of a graphical object. For example, causing for display a visual indicator of a graphical object in response to determining an actionable sepsis-specific criteria and a risk assessment array have been satisfied. Environment 100 includes one or more electronic health record (EHR) (also referred to as electronic medical record) systems, such as hospital EHR system 160, communicatively coupled to network 175, which is communicatively coupled to computer system 120. In some aspects, components of environment 100 that are shown as distinct components may be embodied as part of or within other components of environment 100. For example, EHR systems 160 may comprise one or more EHR systems, such as hospital EHR systems, health information exchange EHR systems, ambulatory clinic EHR systems, psychiatry/neurology EHR systems. Such EHR systems 160 may be implemented in computer system 120. Similarly, EHR system 160 may perform functions for two or more of the EHR systems (not shown).

Network 175 may comprise the Internet and/or one or more public networks, private networks, other communications networks, such as a cellular network, or similar network for facilitating communication among devices connected through the network 175. In some aspects, network 175 may be determined based on factors such as the source and destination of the information communicated over network 175, the path between the source and destination, or the nature of the information. For example, intra-organization or internal communication may use a private network or virtual private network (VPN). Moreover, in some aspects, items shown as being communicatively coupled to network 175 may be directly communicatively coupled to other items shown communicatively coupled to network 175.

In some aspects, operating environment 100 may include a firewall (not shown) between a first component and network 175. In such aspects, the firewall may reside on a second component located between the first component and network 175, such as on a server (not shown), or reside on another component within network 175, or may reside on or as part of the first component.

Aspects of EHR system 160 include one or more data stores of health records, which may be stored on storage 121, and may further include one or more computers or servers that facilitate the storing and retrieval of health records. In some aspects, EHR system 160 may be implemented as a cloud-based platform or may be distributed across multiple physical locations. EHR system 160 may further include record systems that store real time or near real time patient (or user) information, such as wearable, bedside, or in-home patient monitors, for example. Although FIG. 1A depicts an exemplary EHR system 160 that may be used for storing patient information, it is contemplated that an embodiment may also rely on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a GUI operated by a software application or set of applications (e.g., decision support application 140) on a computing device. In an embodiment, the application includes the PowerChart® software manufactured by Cerner Corporation. In an embodiment, the application is a Web-based application or applet. A healthcare provider application may display for a user/clinician the first and/or second visual indicator of the graphical object as described herein. Aspects of user/clinician interface 142 also facilitate accessing and receiving information from a user or healthcare provider about a specific patient or population of patients, including patient history; healthcare resource data; physiological variables (e.g., vital signs) measurements; time series; or other health-related information, and facilitates the display of results, recommendations, or orders, for example.

An embodiment of decision support application 140 comprises a software application or set of applications (which may include programs, routines, functions, or computer-performed services) residing on a client computing device, on one or more servers in the cloud, or distributed in the cloud and on a client computing device, such as a personal computer, laptop, smartphone, tablet, mobile computing device, front-end terminals in communication with back-end computing systems or other computing device(s), such as computing system 120 described below. In an embodiment, decision support application 140 includes a Web-based application or applet (or set of applications) usable to provide or manage user services provided by an embodiment of the invention. In an embodiment, decision support application 140 sends a recommendation or notification (such as a visual indicator of a graphical object) directly to user/clinician interface 142 through network 175. In an embodiment, application 140 sends a notification of a risk of maternal-fetal sepsis to user/clinician interface 142. In some aspects, application 140 includes or is incorporated into a computerized decision support tool, as described herein. Further, some aspects of application 140 utilize user/clinician interface 142. For instance, in one embodiment of application 140, an interface component, such as user/clinician interface 142, may be used to facilitate access by a user (including a clinician/caregiver or patient) to functions or information on monitor 141, such as operational settings or parameters, user identification, user data stored on monitor 141, and diagnostic services or firmware updates for monitor 141, for example.

In some aspects, application 140 and/or interface 142 facilitates accessing and receiving information from a user or health care provider about a specific patient, a set of patients, or a population according to the aspects presented herein. Such information may include historical data; health care resource data; variables measurements; time series; or other health-related information. Application 140 and/or interface 142 also facilitates the display of results, recommendations, or orders, for example.

Decision support application 140 may also be used for providing diagnostic services or evaluation of the performance of various aspects. As shown in example environment 100, in one embodiment, decision support application 140, or the computer system on which it operates, is communicatively coupled to monitor 141 via network 175. In an embodiment, patient monitor 141 communicates directly (or via network 175) to computer system 120 and/or user/clinician interface 142. In an embodiment, monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables. It is also contemplated the clinical or physiological information about a patient or population of patients, such as the monitored variables, patient demographics, patient history, and/or clinical narratives regarding the patient, used according to the embodiment of the invention disclosed herein may be received from a patient's historical data in EHR system 160, or from human measurements, human observations, or automatically determined by sensors in proximity to the patient.

An embodiment of monitor 141 stores user-derived data locally or communicates data over network 175 to be stored remotely. In an embodiment, decision support application 140, or the computer system it is operating on, is wirelessly communicatively coupled to monitor 141. Application 140 may also be embodied as a software application or app operating on a user's mobile device, as described above. In an embodiment, application 140 and monitor 141 are functional components of the same device, such as a device including a sensor, application, and a user interface. In an embodiment, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations, such as one or more local clients and one or more remote servers and may be distributed across the other components of example operating environment 100. For example, a portion of computer system 120 may be embodied on monitor 141 or the computer system supporting application 140 for performing signal conditioning of a measured patient variable. In one embodiment, computer system 120 comprises one or more computing devices, such as a server, desktop computer, laptop, or tablet, cloud-computing device or distributed computing architecture, a portable computing device, such as a laptop, tablet, ultra-mobile PC, or a mobile phone.

Aspects of computer system 120 include computer software stack 125, which, in some aspects, operates in the cloud as a distributed system on a virtualization layer within computer system 120, and includes operating system 129. Operating system 129 may be implemented as a platform in the cloud and is capable of hosting a number of services, such as services 122, 124, 126, and 128, described further herein. Some aspects of operating system 129 comprise a distributed adaptive agent operating system. Aspects of services 122, 124, 126, and 128 run as a local or distributed stack in the cloud, on one or more personal computers or servers, such as computer system 120, and/or a computing device running interface 142 and/or decision support application 140. In some aspects, user/clinician interface 142 and/or decision support application 140 operate in conjunction with software stack 125.

Computation services 126 perform software operations such as determining an actionable sepsis-specific criteria and/or risk assessment array are satisfied. In an embodiment, computation services 126 and records/documents ETL service 124 include computer software services or computer-program routines. Computation services 126 also may include natural language processing services (not shown) such as Discern nCode™ developed by Cerner Corporation, or similar services. In an embodiment, computation services 126 include the services or routines that may be embodied as one or more software agents or computer software routines.

In some aspects, stack 125 includes file system or cloud-services 128. Some aspects of file system/cloud-services 128 may comprise an Apache Hadoop and Hbase framework or similar frameworks operable for providing a distributed file system and which, in some aspects, provide access to cloud-based services, such as those provided by Cerner HealtheIntent®. Additionally, some aspects of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some aspects of the invention also may be used in conjunction with Cerner Millennium®, Cerner CareAware® (including CareAware iBus®), Cerner CareCompass®, Cerner FetaLink+®, or similar products and services.

Example operating environment 100 also includes storage 121 (or data store 121), which, in some aspects, includes patient information for a candidate or target patient (or information for multiple patients), including raw and processed patient information; variables associated with patient recommendations; recommendation knowledge base; recommendation rules; recommendations; recommendation update statistics; an operational data store, which stores events, frequent item sets (such as "X often happens with Y", for example), and item sets index information; association rulebases; agent libraries, solvers and solver libraries, and other similar information, including data and computer-usable instructions; patient-derived data; and healthcare provider information, for example. For example, storage 121 may include the maternal patient information, as described herein.

Additionally, it is contemplated the term "data" used herein includes any information that can be stored in a computer storage device or system, such as user-derived data, computer-usable instructions, software applications, or other information. In some aspects, storage 121 comprises data store(s) associated with EHR system 160. Further, although depicted as a single storage store, storage 121 may comprise one or more data stores, or may be in the cloud.

Figure 1B:
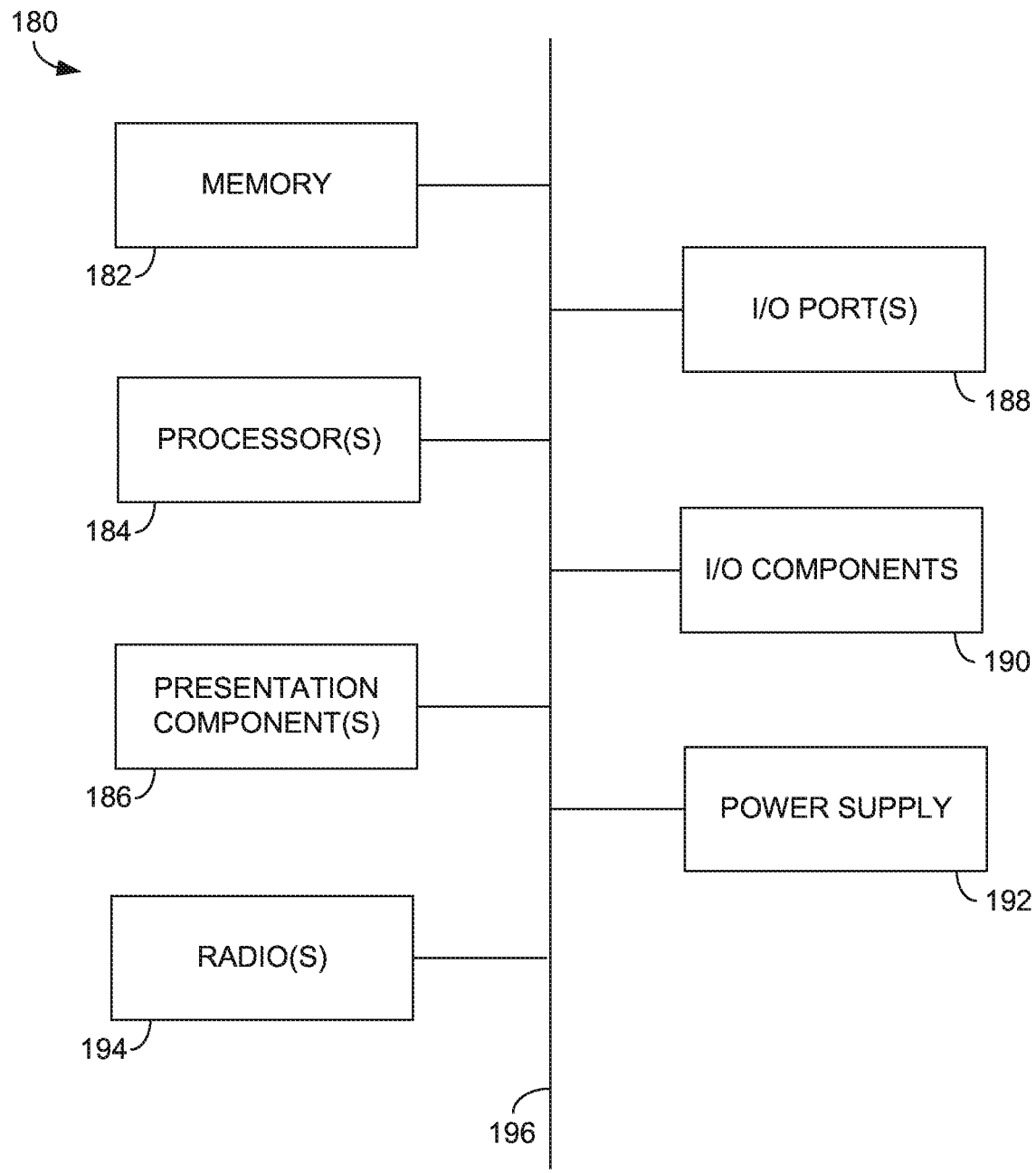

Turning briefly to FIG. 1B, there is shown one example embodiment of computing system 180 representative of a system architecture that is suitable for computer systems such as computer system 120. Computing system 180 includes a bus 196 that directly or indirectly couples the following devices: memory 182; one or more processors 184; one or more presentation components 186; input/output (I/O) ports 188; input/output components 190; radio 194; and an illustrative power supply 192. Bus 196 represents what may be one or more busses (such as an address bus, data bus, or combination thereof). Although the various blocks of FIG. 1A are shown with lines for the sake of clarity, in reality, delineating various components is not so clear, and metaphorically, the lines would more accurately be grey and fuzzy. For example, one may consider a presentation component, such as a display device, to be an I/O component. However, processors also have memory. As such, the diagram of FIG. 1A is merely illustrative of an exemplary computing system that can be used in connection with one or more aspects of the present invention. Distinction is not made between such categories as "workstation," "server," "laptop," "hand-held device," etc., as all are contemplated within the scope of FIG. 1A and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information, such as computer-readable instructions, data structures, program modules, or other data. Computer storage media includes, but is not limited to, RAM; ROM; EEPROM; flash memory or other memory technology; CD-ROM; digital versatile disks (DVD); or other optical disk storage, magnetic cassettes, magnetic tape, magnetic disk storage or other magnetic storage devices; or any other medium which can be used to store the desired information and which can be accessed by computing system 180. Computer storage media does not comprise signals per se. Communication media typically embodies computer-readable instructions; data structures; program modules; or other data in a modulated data signal, such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared and other wireless media. Combinations of any of the above should also be included within the scope of computer-readable media.

Memory 182 includes computer storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities, such as memory 182 or I/O components 190. Presentation component(s) 186 present data indications to a user or other device, for example, via a GUI. Exemplary presentation components include a display device, speaker, printing component, vibrating component, etc.

In some aspects, computing system 180 comprises radio(s) 194 that facilitates communication with a wireless telecommunications network. Illustrative wireless telecommunications technologies include CDMA, GPRS, TDMA, GSM, and the like. Radio(s) 194 may additionally or alternatively facilitate other types of wireless communications including Wi-Fi, WiMAX, LTE, or other VoIP communications. As can be appreciated, in various aspects, radio(s) 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition; stylus recognition; facial recognition; biometric recognition; gesture recognition both on screen and adjacent to the screen; air gestures; head and eye tracking; and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some aspects, computer system 120 is a computing system made up of one or more computing devices. In some aspects, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system; a data processing system; a centralized computing system; a single computer, such as a desktop or laptop computer; or a networked computing system.

Figure 2:
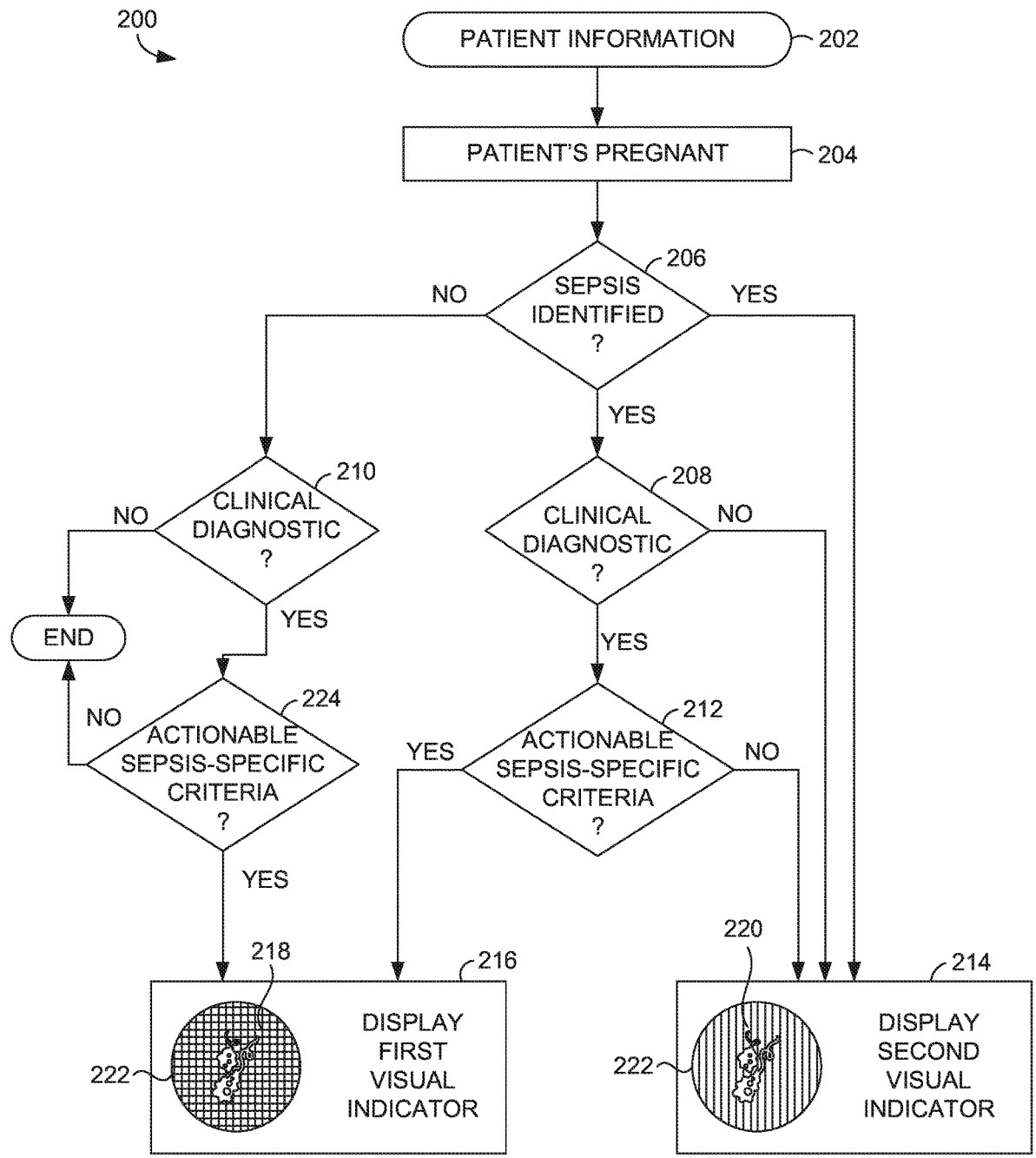
FIG. 2 is a flow diagram of an exemplary method of determining a risk of maternal-fetal sepsis, in accordance with aspects of the present invention.

Turning now to FIG. 2, a flow diagram of an exemplary method of determining a risk of maternal-fetal sepsis is provided and referred to generally as method 200. In particular, example method 200 may be performed by one or more non-transitory computer storage media having computer-executable instructions embodied thereon that, when executed, perform a method for detecting maternal-fetal sepsis. In some aspects, the method 200 is suitable for implementation as a computer-performed decision support tool, or as an application for providing care to patients including for the treatment of maternal-fetal sepsis.

In accordance with method 200, at block 202, patient information is received for the patient. In some aspects, the patient information includes historical patient information, or current patient information. In some exemplary aspects, current patient information includes data relating to the patient's labs; vitals, diagnoses; and medications from prior encounters and from the current encounter (e.g., the current admission to a healthcare facility, or current period of receiving home healthcare services). The current encounter information may include a diagnosis and/or treatment (including medications administered or ordered and procedures performed or ordered). During the current encounter, the patient may be diagnosed or treated with a condition such as an infection. Current patient information may include lab results, including vital sign data.

In some aspects, patient information may include patient demographic data. Patient demographics may include age, sex, race, nationality, socioeconomic status, marital status, and/or employment status. This data may further include the patient's insurance information, such as the insurance provider and the type of plan. In some aspects, patient demographic information is not directly used to determine a risk of maternal-fetal sepsis.

This patient information may be received from different sources. For instance, in one embodiment, all patient information is received at block 202 from the patient's EMR. In other aspects, data relating to the patient's current condition and/or patient demographics may be received directly from a user, such as the patient or a care provider. For example, the care provider (e.g., clinician) may input patient information into a device. Some current patient information, such as patient variable values, may be received from one or more sensors or monitoring devices or directly from a laboratory running the laboratory procedures. Additionally, historical patient information may be received from the patients EMR and/or from insurance claims data for the patient. For example, EMR data from in-home care services, hospitals or any healthcare facility may be received. In an alternative embodiment, the patient's history may be received directly from the patient, such as during registration when the patient is admitted to a hospital or care facility for the current encounter or starting the current care services.

At block 204, method 200 includes determining the patient is or was pregnant within a specified time interval. The determination may be based on the patient information received at block 202. In some aspects, the patient may not be pregnant but the system may proceed to block 206. As described herein, maternal-fetal sepsis can be an issue for patients during pregnancy, or during labor, the condition is referred to as "maternal-fetal sepsis". Therefore, at block 204 the patient may be determined to be pregnant, or in labor.

At block 206, the method 200 includes determining if a risk of maternal-fetal sepsis is identified. In some aspects, this may include determining a risk assessment array for the patient has been satisfied. In some aspects, block 206 may include generating a risk assessment array for the patient. The risk assessment array may include the patient's risk of maternal-fetal sepsis based on the maternal patient information. A patient's risk of maternal-fetal sepsis may be based on a symptom or condition indicative of maternal-fetal sepsis. A patient's risk of maternal-fetal sepsis may include vitals above a threshold. For example, the patient may have an elevated temperature (e.g., above a threshold) and/or an elevated white blood cell count (e.g., above a threshold). Other potential conditions for identifying a risk of maternal-fetal sepsis may be any information from the patient information. For example, a respiratory rate, blood pressure, peripheral capillary oxygen saturation (SpO2), or heart rate may be above a threshold. Maternal-fetal sepsis may be identified by computation service 126 (described in FIG. 1A) and determine the risk assessment array is satisfied. The risk assessment array may be satisfied if one or a plurality of conditions indicative of maternal-fetal sepsis are met, as described herein.

At block 208, the method 200 includes receiving a clinical diagnostic for the patient. The clinical diagnostic may represent if the organisms associated with maternal-fetal sepsis are present in the patient's bloodstream. For example, the clinical diagnostic may be a laboratory result.

At block 210, the method 200 includes receiving a clinical diagnostic for the patient, similar to block 208. As illustrated, if at block 206 a risk of maternal-fetal sepsis is not identified, the method 200 may proceed to block 210, including receiving a clinical diagnostic for the patient. If no clinical diagnostic is received, the method 200 may terminate.

At block 212, the method 200 includes determining if an actionable sepsis-specific criteria has been satisfied. The actionable sepsis-specific criteria may be any indication a remedial action should be made to treat maternal-fetal sepsis in the patient i.e., mother and fetal. The actionable sepsis-specific criteria may be based on the clinical diagnostic received at block 208. For example, in some aspects the actionable sepsis-specific criteria may be satisfied if the clinical diagnostic represents organisms associated with maternal-fetal sepsis are present in the patient's bloodstream. In some aspects, the computation service 126 (described in FIG. 1A) may determine the actionable sepsis-specific criteria has been satisfied.

At blocks 214 and 216, the method 200 includes causing for display first and second visual indicators. The first and second visual indicators may be a second visual indicator of a graphical object, described herein. The first and second visual indicators are a visual indicator as described herein. Each of blocks 214 and 216 illustrate an exemplary first visual indicator 218 and an exemplary second visual indicator 220 of an exemplary graphical object 222. The exemplary graphical object 222 is represented as an icon of a maternal-fetal sepsis related organism. The visual indicator of the graphical object may be caused for display as a notification or an alert. The visual indicator of the graphical object may indicate a risk of maternal-fetal sepsis. For example, and as described herein, the first visual indicator 218 may be illustrated when block 212 is satisfied, and the first visual indicator 218 may indicate an actionable sepsis-specific criteria has been satisfied. The second visual indicator 214 may be illustrated when block 212 is determined not to be satisfied, and the second visual indicator may illustrate that blocks 206 and/or 208 have been satisfied.

The first and second visual indicators are not the same visual indicator of the graphical object. In some aspects, each visual indicator may be a transformation and/or augmentation of the graphical object. In some aspects, each visual indicator may variegate the graphical object. For example, the first visual indicator may be a red color of the graphical object and the second visual indicator may be a yellow color of the graphical object.

At block 210, if a clinical diagnostic is received, the method 200 may proceed to block 224. Block 224, similar to block 212, may determine if an actionable sepsis-specific criteria has been satisfied. If no actionable sepsis-specific criteria has been satisfied, then the method 200 may terminate. Further, if an actionable sepsis-specific criteria has been satisfied, the method 200 may proceed to block 216.

As illustrated in FIG. 2, the method 200 may receive patient information at block 202, and proceed to determine the patient is pregnant at block 204. At block 206, a risk of maternal-fetal sepsis is identified in the patient. If a risk of maternal-fetal sepsis is identified at block 206, the method 200 may proceed to block 214 to cause to display a second visual indicator and/or block 208 to receive a clinical diagnostic.

For example, if maternal-fetal sepsis is identified, the second visual indicator may be caused to be displayed. A clinician can view the second visual indicator and may more closely monitor the patient. The clinician, in response to the second visual indicator may even request a clinical diagnostic for the patient to confirm if an actionable sepsis-specific criteria has been satisfied. In this way, the method 200 can help identify maternal-fetal sepsis early and increase the odds of survival of the patient.

In some aspects, the method 200 may not execute blocks 214 or 216. It may be determined at block 206 a risk of maternal-fetal sepsis was not identified in the patient and the method 200 may proceed to block 210 to receive a clinical diagnostic. If no clinical diagnostic is received, the method 200 may end without generating a first visual indicator 218 or a second visual indicator 220 of the graphical object 222. Block 210 is different than block 208, where if no clinical diagnostic was received at block 208, the method 200 may execute block 214 and cause for display the second visual indicator. At block 210, the method may not execute the second visual indicator. If a clinical diagnostic is received at block 210, and at block 224 the actionable sepsis-specific criteria may be determined to be satisfied, the method may display the first visual indicator at block 216. For example, if a patient has an undetected risk of maternal-fetal sepsis (e.g., not identified at block 206), but a diagnostic test is ordered, the system may cause for display the first visual indicator 218.

If maternal-fetal sepsis is identified at block 206, the second visual indicator may be caused to be displayed, and the method 200 may continue to block 208. If a clinical diagnostic is not received at block 208, the method 200 may still display the second visual indicator to notify a clinician a risk of maternal-fetal sepsis was identified at block 206. If the clinical diagnostic is received at block 208, an actionable sepsis-specific criteria may be determined at block 212. Dependent on whether the actionable sepsis-specific criteria is satisfied, the method 200 may proceed to block 214 or 216.

In some aspects, when blocks 206, 208, and/or 212 execute block 214 to cause to display the second visual indicator, and an actionable sepsis-specific criteria is satisfied, the method 200 may execute block 216 subsequent to block 214. For example, in some aspects the method 200 may determine a risk of maternal-fetal sepsis at block 206 and subsequently execute blocks 214 and 208, described herein. In another example, the second visual indicator may be on the GUI. When block 216 is executed, block 216 may cause to change on the GUI the second visual indicator, generated by block 214, to a first visual indicator of the graphical object. Stated differently, at block 216 on the GUI the second visual indicator may be changed to a first visual indicator of the graphical object. For example, changing on the GUI the second visual indicator to a first visual indicator may comprise a transformation of the graphical object. In another example, changing on the GUI the second visual indicator to a first visual indicator may comprise an augmentation of the graphical object. In yet another example, changing on the GUI the second visual indicator to a first visual indicator may comprise variegating the graphical object. In one embodiment, the second visual indicator may be a first color (e.g., yellow) and the first visual indicator may be a second color (e.g., red).

In some embodiments, the method 200 may execute additional blocks to cause for display additional information beyond the first or second visual indicators 218 and 220. In some embodiments, and as described herein, the risk assessment array, patient information, clinical diagnostic, and/or remedial actions may be displayed simultaneously and/or in real time with the first or second visual indicators 218 and 220. For example, the remedial actions may be displayed simultaneously with life-saving medical interventions, such as fluid resuscitation or vital organ support.

In some embodiments, the method 200 may execute additional blocks to remove the first or second visual indicators 218 and 220 from the GUI. For example, in some embodiments, the method 200 may determine pregnancy is no longer active in the patient, and the method 200 may not display the first or second visual indicators 218 and 220.

As stated, in exemplary aspects, the first and second visual indicators of the graphical object may be caused to be displayed on a GUI. The GUI, in some aspects, may be displayed on a mobile device, monitor, or other display. FIGS. 3A-3B and 4-5 are an exemplary screen display of a visual indicator of a graphical object for maternal-fetal sepsis, in accordance with aspects of the present invention.

Figure 3A:
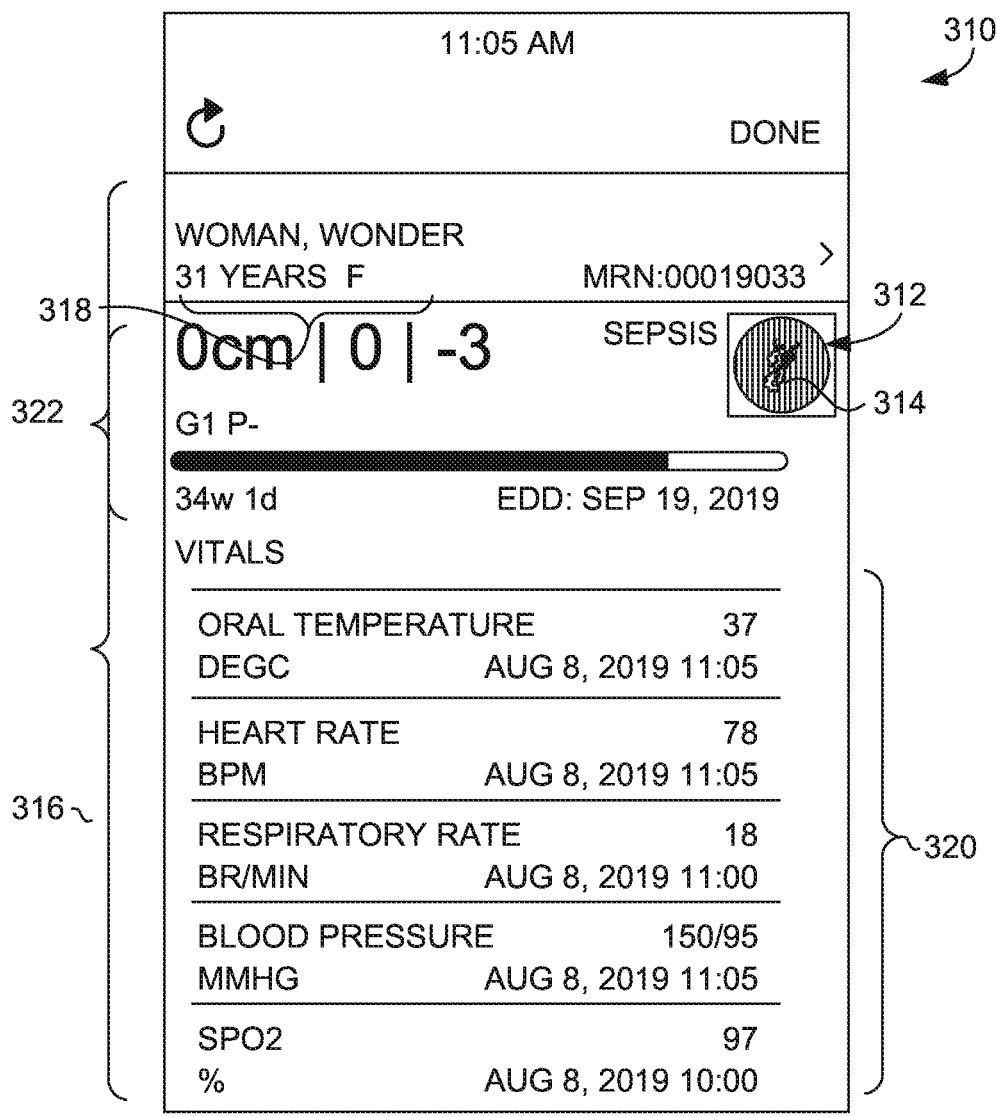

FIG. 3A illustrates an exemplary screen display 310. A second visual indicator 314 of the graphical object 312 is shown on the exemplary screen display 310. The second visual indicator 314 of the graphical object 312 may display an identified risk of maternal-fetal sepsis. Simultaneously displayed with the second visual indicator 314 is patient information 316. In some aspects, the patient information 316 may be displayed in real time on the GUI with the second visual indicator 314 or a first visual indicator, described herein.

The patient information may include demographic information 318, vitals 320, and delivery data 322. Demographic information 318 may include the patient's age, gender, ethnicity, and/or other sectors of a population. In some aspects the vitals 320 may be vitals from a current pregnancy of the patient. The vitals 320 may be any clinical measure. For example, and as illustrated in FIG. 3A, vitals 320 include oral temperature, heart rate, respiratory rate, blood pressure, and/or SPO2 percentage. In some embodiments, patient information 316 may include delivery data 322. Delivery data 322 may include specific information about delivery of a baby. For example, delivery data 322 may include an expected delivery date, length of pregnancy, effacement data, dilation percentage, and station.

The patient information 316 may satisfy a risk assessment array for the patient. In aspects, if the risk assessment array is satisfied, the second visual indicator 314 of the graphical object 312 may be caused for display.

Figure 3B:
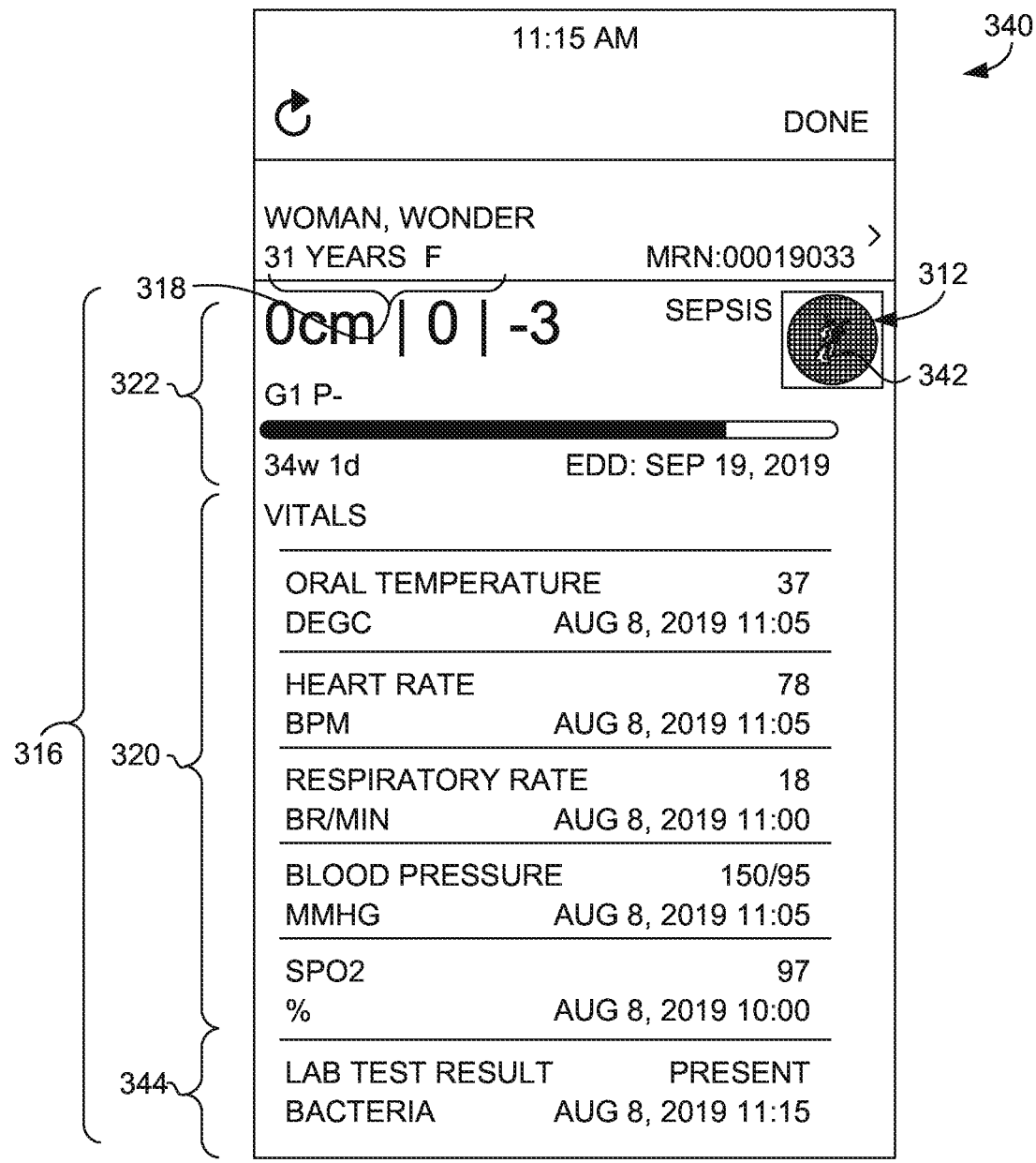

FIG. 3B illustrates an exemplary screen display 340. A first visual indicator 342 of the graphical object 312 is shown on the exemplary screen display 340. The first visual indicator 342 of the graphical object 312 may display the actionable sepsis-specific criteria and/or the risk assessment array have been satisfied. Simultaneously displayed with the first visual indicator 342 of the graphical object 312 is patient information 316 and a clinical diagnostic 344.

The clinical diagnostic 344 illustrates one embodiment of the clinical diagnostic 344, such as a lab result. The lab result illustrates bacteria are present in the patient's bloodstream. This clinical diagnostic 344 may satisfy the actionable sepsis-specific criteria. In this embodiment, in response to the actionable sepsis-specific criteria, the first visual indicator 342 of the graphical object 312 may have been caused for display.

FIG. 4 illustrates another exemplary screen display 400. The screen display 400 includes a second visual indicator 402 of a graphical object 404. The second visual indicator 402 of the graphical object 404 displays the risk assessment array may be satisfied, as described herein. Simultaneously displayed with the second visual indicator 402 of the graphical object 404 is patient information 406. The patient information 406 includes data from an active pregnancy in a "current pregnancy" tab and a "contact information" tab. The exemplary screen display 400 may be displayed to a clinician, where the second visual indicator 402 of the graphical object 404 may alert the clinician of the patient's risk of maternal-fetal sepsis.

FIG. 5 illustrates another exemplary screen display 500. The screen display 500 includes a second visual indicator 504 of a graphical object 502. Simultaneously displayed with the second visual indicator 504 of the graphical object 502 is patient information 506. The exemplary screen display 500 may be displayed to a clinician, where the second visual indicator 504 of the graphical object 502 may alert the clinician of the patient's risk of maternal-fetal sepsis.

Although in FIGS. 4 and 5 a second visual indicator 402 and 504 is displayed, in some aspects a first visual indicator may be displayed when an actionable sepsis-specific criteria has been satisfied. Additional details regarding determining an actionable sepsis-specific criteria or a risk assessment array have been satisfied are discussed with respect to method 200 of FIG. 2.

Figure 6:
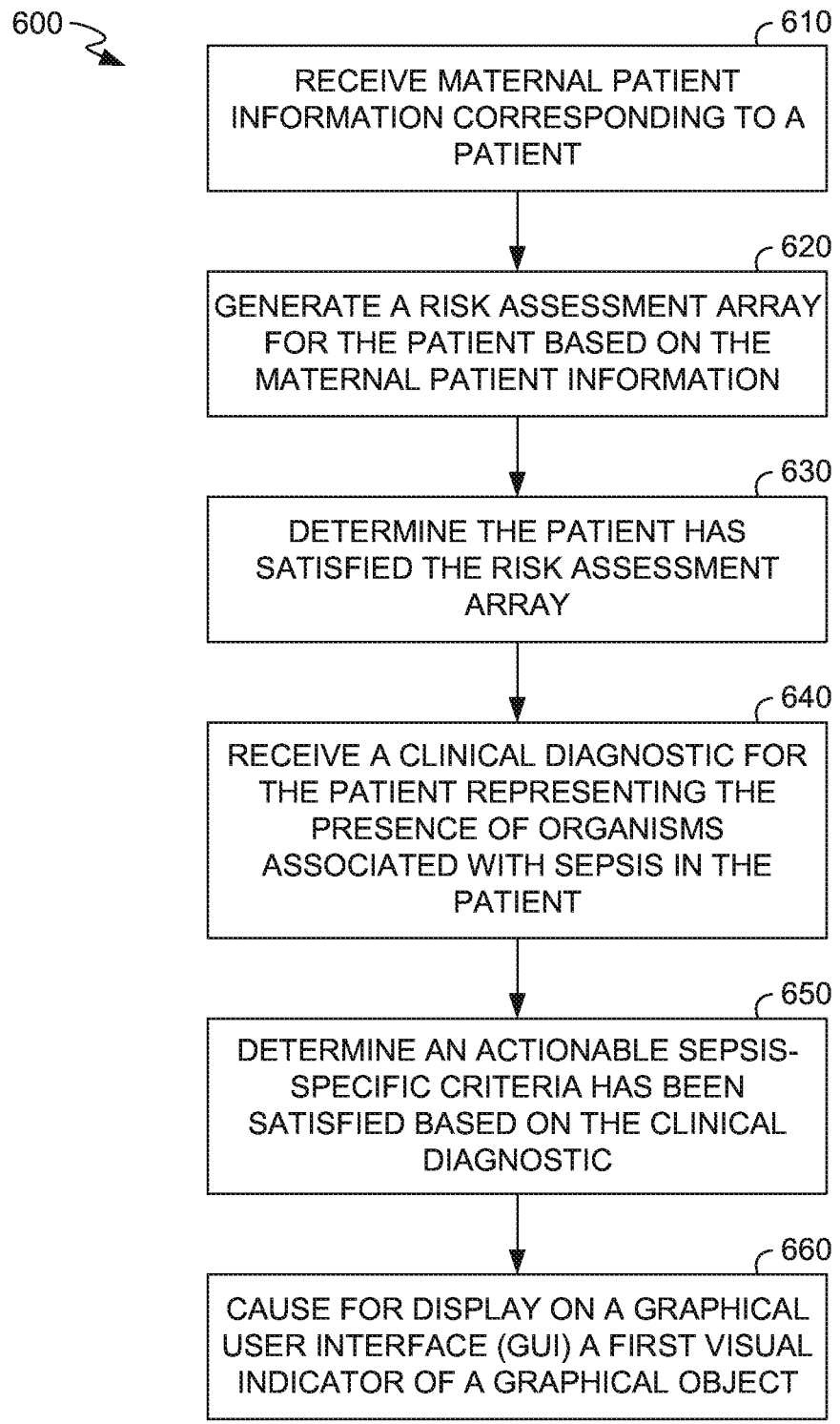
FIG. 6 is a flow diagram showing an example of a method for determining a risk of maternal-fetal sepsis and causing for display a visual indicator, in accordance with aspects of the present disclosure.

FIG. 6 is a flow diagram showing an example of a method 600 for determining a risk of maternal-fetal sepsis and causing for display a visual indicator, in accordance with aspects of the present disclosure. Method 600 may be performed by any computing device (such as computing device described with respect to FIGS. 1A and 1B).

Initially, at block 610 maternal patient information corresponding to a patient is received. For example, the patient information may be received from a source. In one embodiment, the method 600 may include receiving, from a source, maternal patient information corresponding to a patient. Additionally or alternatively, the maternal patient information may comprise vitals from a current pregnancy of a patient. Additionally or alternatively, the maternal patient information may be vitals received in near real time from a current pregnancy of the patient.

At block 620, the method 600 includes a risk assessment array for the patient based on the maternal patient information generated. For example, the method 600 includes generating a risk assessment array for the patient representing the patient's risk of maternal-fetal sepsis based on the maternal patient information.

At block 630, the method 600 includes determine the patient has satisfied the risk assessment array. For example, the method 600 includes determining the patient has satisfied the risk assessment array. In some aspects, the risk assessment array may be determined to be satisfied if the maternal patient information is above a threshold.

At block 640, the method 600 includes a clinical diagnostic for the patient representing the presence of organisms associated with maternal-fetal sepsis in the patient is received. For example, the method 600 includes receiving a clinical diagnostic for the patient representing the presence of organisms associated with maternal-fetal sepsis in the patient. In some aspects the clinical diagnostic may be a laboratory test result.

At block 650, the method 600 includes an actionable sepsis-specific criteria has been satisfied based on the clinical diagnostic determined. For example, the method 600 includes determining an actionable sepsis-specific criteria has been satisfied based on the clinical diagnostic. In some aspects the clinical diagnostic may satisfy the actionable sepsis-specific criteria when the presence of organisms associated with maternal-fetal sepsis are found to be present in the patient's blood.

At block 660, the method 600 includes cause for display on a GUI a first visual indicator of a graphical object. For example, causing for display on a GUI a first visual indicator of a graphical object in response to determining the actionable sepsis-specific criteria and the risk assessment array have been satisfied. Alternatively or additionally, the method 600 may further cause for display a second visual indicator of the graphical object in response to determining the patient has satisfied the risk assessment array. Additionally or alternatively, the first visual indicator of the graphical object is caused to change the second visual indicator of the graphical object on the GUI. In some aspects, further caused for display on the GUI is data representative of the clinical diagnostic. In some aspects the maternal patient information may be caused to simultaneously display the maternal patient information on the GUI.

Figure 7:
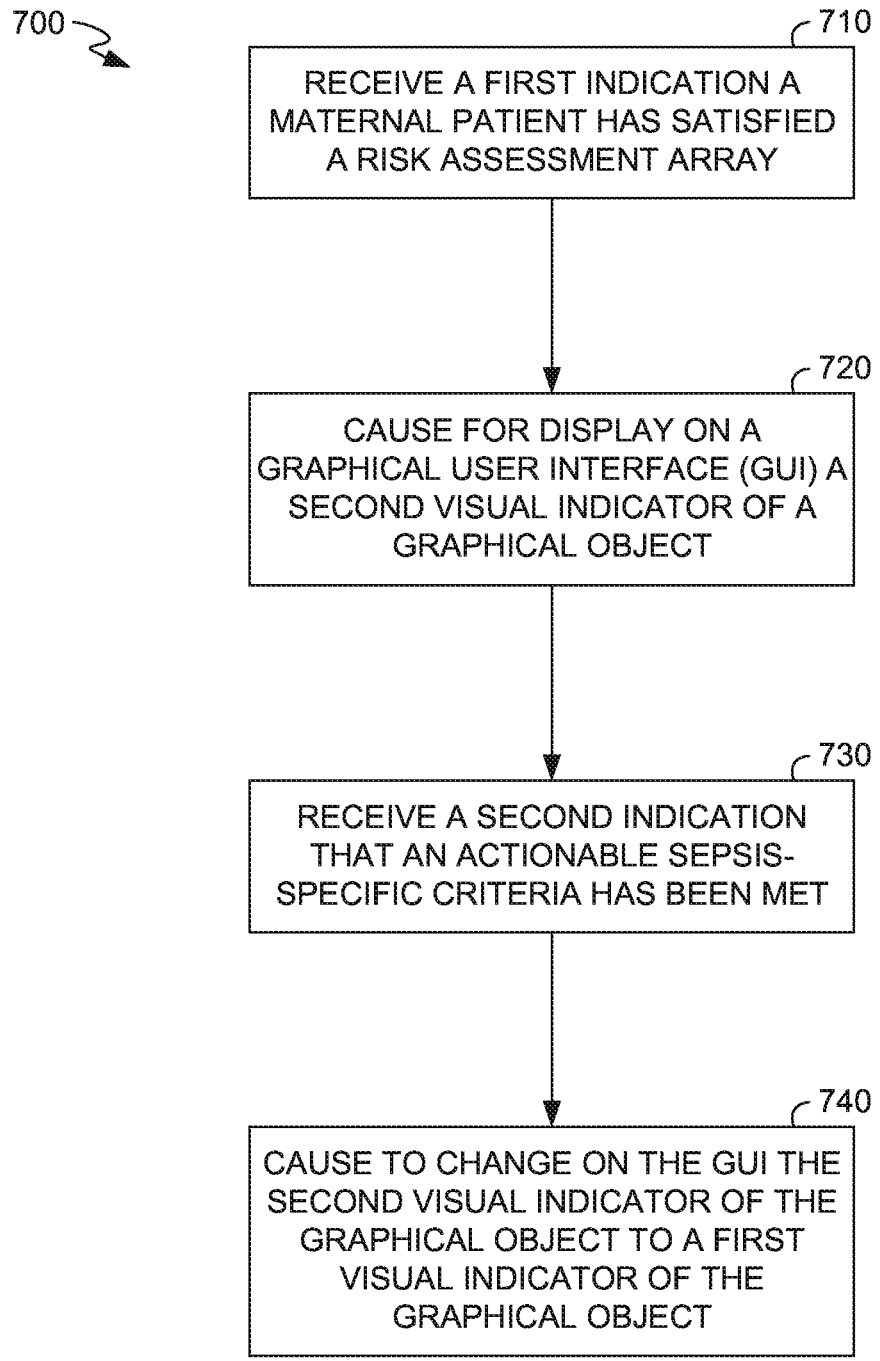
FIG. 7 is a flow diagram showing an example of a method of receiving an indication for maternal-fetal sepsis and providing a visual indicator, in accordance with aspects of the present disclosure.

FIG. 7 is a flow diagram showing an example of a method 700 of receiving an indication for maternal-fetal sepsis and providing a visual indicator. Method 700 may be performed by any computing device, such as computing device described with respect to FIGS. 1A and 1B.

At block 710, the method 700 includes receiving a first indication a maternal patient has satisfied a risk assessment array. For example, receiving a first indication a maternal patient has satisfied a risk assessment array for the maternal patient's risk of maternal-fetal sepsis based on a maternal patient information. In some aspects, as described, a risk assessment array may be determined to be satisfied by a remote system, server, service, or manually input into the system (e.g., a clinician may determine the risk assessment array is satisfied). Additionally or alternatively, the risk assessment array may be determined to be satisfied using the methods described in method 200 of FIG. 2. Additionally or alternatively, the maternal patient information may comprise vitals from a current pregnancy of the patient.

At block 720, the method 700 includes cause for display on a GUI a second visual indicator of a graphical object. For example, causing for display on a GUI a second visual indicator of a graphical object in response to the first indication. For example, the first indication may cause for display on the GUI a second visual indicator.

At block 730, the method 700 includes receiving a second indication that an actionable sepsis-specific criteria has been met. For example, receiving a second indication that an actionable sepsis-specific criteria has been met based on a clinical diagnostic for the maternal patient representing a presence of organisms associated with maternal-fetal sepsis in the maternal patient. In some aspects, as described, the actionable sepsis-specific criteria may be determined to be satisfied by a remote system, server, service, or manually input into the system (e.g., a clinician may determine the actionable sepsis-specific criteria is satisfied). Additionally or alternatively, the actionable sepsis-specific criteria may be determined using the methods described in method 200 of FIG. 2.

At block 740, the method 700 includes causing to change on the GUI the second visual indicator of the graphical object to a first visual indicator of the graphical object. For example, causing to change on the GUI the second visual indicator of the graphical object to a first visual indicator of the graphical object in response to receiving the second indication. In some aspects the method 700 may include causing for display on the GUI data representative of the clinical diagnostic and the maternal patient information simultaneously with the graphical object in near real time. Additionally or alternatively, changing on the GUI the second visual indicator to the first visual indicator of the graphical object may include at least one of a transformation, augmentation, and variegating the graphical object.

Figure 8:
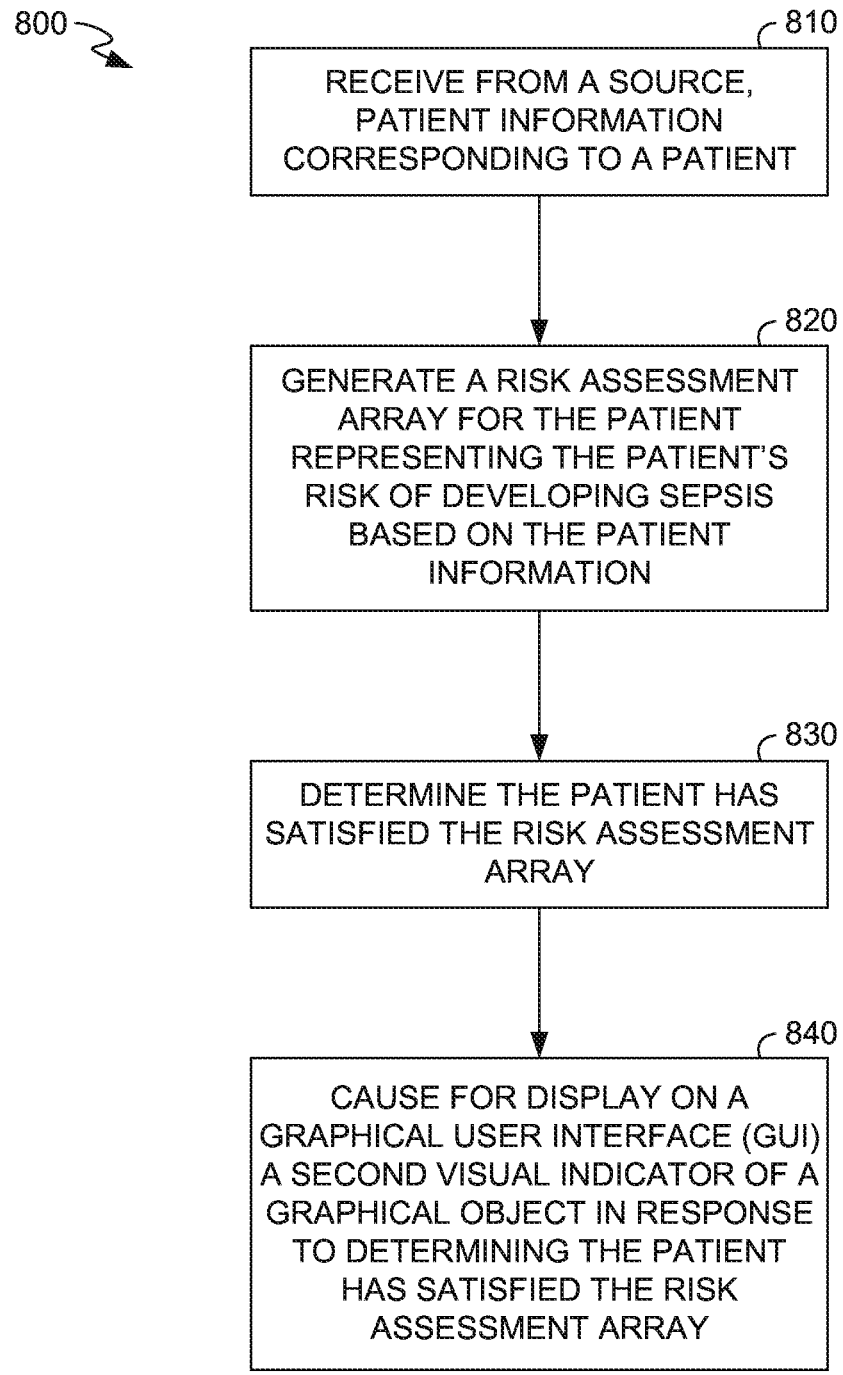
FIG. 8 is a flow diagram showing an example of determining a risk of maternal-fetal sepsis and causing for display a visual indicator, in accordance with aspects of the present disclosure.

FIG. 8 is a flow diagram showing an example of determining a risk of maternal-fetal sepsis and causing for display a visual indicator, in accordance with aspects of the present disclosure. Method 800 may be performed by any computing device, such as computing device described with respect to FIGS. 1A and 1B.

At block 810, the method 800 may include receiving from a source, patient information corresponding to a patient. For example, receiving from a source patient information corresponding to a patient. In some aspects, the patient information may include vitals received in near real time from a current pregnancy of the patient. Alternatively or additionally, the vitals received may comprise at least one of oral temperature, heart rate, respiratory rate, blood pressure, SpO2, and cervix effacement.

At block 820, the method 800 may include generate a risk assessment array for the patient representing the patient's risk of maternal-fetal sepsis based on the patient information. For example, generating a risk assessment array for the patient representing the patient's risk of maternal-fetal sepsis based on the patient information.

At block 830, the method 800 may include determine the patient has satisfied the risk assessment array.

At block 840, the method 800 may include cause for display on a GUI a second visual indicator of a graphical object in response to determining the patient has satisfied the risk assessment array. Additionally or alternatively, the method 800 may include receiving a clinical diagnostic for the patient representing the presence of organisms associated with maternal-fetal sepsis in the patient, determining an actionable sepsis-specific criteria has been satisfied based on the clinical diagnostic, and causing to change on the GUI the second visual indicator of the graphical object to a first visual indicator of the graphical object in response to determining the actionable sepsis-specific criteria has been satisfied.

Many different arrangements of the various components depicted, as well as components not shown, are possible without departing from the spirit and scope of the present invention. It will be understood that certain features and sub-combinations are of utility and may be employed without reference to other features and sub-combinations and are contemplated within the scope of the claims. Not all steps listed in the various figures need to be carried out in the specific order described. Accordingly, the scope of the invention is intended to be limited only by the following claims.

What is claimed is:

1. One or more non-transitory computer storage media having computer-executable instructions embodied thereon that, when executed, cause operations for detecting maternal-fetal sepsis, the operations comprising:

receiving, from a source, maternal patient information corresponding to a patient;

generating a risk assessment array for the patient, the risk assessment array representing the patient's risk of maternal-fetal sepsis based on the maternal patient information;

determining that the risk assessment array has been satisfied based on the maternal patient information;

in response to determining that the risk assessment array has been satisfied, causing display on a graphical user interface (GUI) of a first visual indicator of a graphical object, the first visual indicator comprising a set of vertical lines;

identifying a clinical diagnostic associated with the patient, the clinical diagnostic representing a presence of organisms associated with maternal-fetal sepsis in the patient;

determining that an actionable sepsis-specific criteria has been satisfied based on the clinical diagnostic; and in response to determining that both the actionable sepsis-specific criteria and the risk assessment array have been satisfied, causing a transformation of the first visual indicator to a second visual indicator in the graphical user interface, the transformation (a) retaining the set of vertical lines, from the first visual indicator, that represents the satisfaction of the risk assessment array for the patient's risk of maternal-fetal sepsis, and (b) augmenting the set of vertical lines with a set of horizontal lines that represent the actionable sepsis-specific criteria.

2. The computer storage media of claim 1, wherein the operations further comprise modifying a display on the GUI in response to determining a change in pregnancy status associated with the patient.

3. The computer storage media of claim 2, wherein the second visual indicator of the graphical object is caused to change the first visual indicator of the graphical object on the GUI.

4. The computer storage media of claim 1, wherein the operations further comprise causing display on the GUI of data representative of the clinical diagnostic simultaneously with the graphical object.

5. The computer storage media of claim 1, wherein the maternal patient information comprises vitals associated with a current pregnancy of the patient.

6. The computer storage media of claim 5, wherein the operations further comprise causing display on the GUI of the maternal patient information simultaneously with the graphical object.

7. The computer storage media of claim 1, wherein the operations further comprise causing display of remedial actions based on the actionable sepsis-specific criteria.

8. The computer storage media of claim 1, wherein the maternal patient information comprises vitals received in near real-time and associated with a current pregnancy of the patient.

9. The computer storage media of claim 1, wherein determining that the risk assessment array has been satisfied is based further on at least one adaptive agent trained to determine satisfaction of the risk assessment array.

10. The computer storage media of claim 9, wherein:

the at least one adaptive agent comprises a distributed adoptive agent; and the actionable sepsis-specific criteria is determined to be satisfied using the distributed adaptive agent.

11. The computer storage media of claim 1, wherein:
the set of vertical lines are intersected, by multiple parallel lines, in the second visual indicator but not in the first visual indicator.

12. The computer storage media of claim 1, wherein:
the set of horizontal lines is displayed over the set of vertical lines in the second visual indicator but not in the first visual indicator; and
the operations further comprise causing display on the GUI of data representative of the clinical diagnostic simultaneously with the graphical object.

13. The computer storage media of claim 1, wherein the set of vertical lines of the first visual indicator are superimposed over the graphical object.

14. The computer storage media of claim 13, wherein the graphical object comprises an image depicting a condition of the patient.

15. The computer storage media of claim 1, wherein the set of horizontal lines of the second visual indicator are superimposed over the graphical object.

16. The computer storage media of claim 15, wherein the graphical object comprises an image depicting a condition of the patient.

17. The computer storage media of claim 1, wherein the operations further comprise:
removing from display on the GUI one or both of the first visual indicator or the second visual indicator in response to determining pregnancy is no longer active in the patient.

18. The computer storage media of claim 1, wherein:
the graphical object includes an image depicting a maternal-fetal sepsis related organism; and
one or both of the set of horizontal lines or the set of vertical lines are superimposed over the image.

19. A method for detecting maternal-fetal sepsis, the method comprising:
receiving a first indication that a risk assessment array associated with a maternal patient's risk of maternal-fetal sepsis has been satisfied based on maternal patient information;
in response to the first indication, causing display on a graphical user interface (GUI) of a first visual indicator of a graphical object, the first visual indicator comprising a set of vertical lines;
receiving a second indication that an actionable sepsis-specific criteria has been satisfied based on a clinical diagnostic associated with the maternal patient, the clinical diagnostic representing a presence of organisms associated with maternal-fetal sepsis in the maternal patient; and
in response to receiving the second indication, causing a transformation of the first visual indicator to a second visual indicator on the graphical user interface, the transformation (a) retaining the set of vertical lines, from the first visual indicator, that represents the satisfaction of the risk assessment array for the patient's risk of maternal-fetal sepsis, and (b) augmenting the set of vertical lines with a set of horizontal lines that represent the actionable sepsis-specific criteria.

20. The method of claim 19, further comprising causing display on the GUI of data representative of the clinical diagnostic and of the maternal patient information simultaneously with the graphical object in near real-time.

21. The method of claim 19, wherein the maternal patient information comprises vitals associated with a current pregnancy of the patient.

22. The method of claim 19, wherein changing the first visual indicator to the second visual indicator comprises at least one of a transformation or a variegation of the graphical object.

23. A system comprising:
one or more processors: and
one or more computer-storage media having one or more instructions stored that, when used by the one or more processors, cause the one or more processors to perform operations comprising:
receiving, from a source, patient information corresponding to a patient;
generating a risk assessment array for the patient, the risk assessment array representing the patient's risk of maternal-fetal sepsis based on the patient information;
determining that the risk assessment array has been satisfied based on the patient information;
in response to determining that the risk assessment array has been satisfied, causing display on a graphical user interface (GUI) of a first visual indicator of a graphical object, the first visual indicator comprising a set of vertical lines;
identifying a clinical diagnostic associated with the patient, the clinical diagnostic representing a presence of organisms associated with maternal-fetal sepsis in the patient;
determining that an actionable sepsis-specific criteria has been satisfied based on the clinical diagnostic; and
in response to determining that both the actionable sepsis-specific criteria and the risk assessment array have been satisfied, causing a transformation of the first visual indicator to a second visual indicator in the graphical user interface, the transformation (a) retaining the set of vertical lines, from the first visual indicator, that represents the satisfaction of the risk assessment array for the patient's risk of maternal-fetal sepsis, and (b) augmenting the set of vertical lines with a set of horizontal lines that represent the actionable sepsis-specific criteria.

24. The system of claim 23, the operations further comprising causing display on the GUI of the patient information simultaneously with the graphical object.

25. The system of claim 23, wherein the patient information comprises vitals received in near real-time and associated with a current pregnancy of the patient.

26. The system media of claim 25, wherein the vitals comprise at least one of oral temperature, heart rate, respiratory rate, blood pressure, SpO2, or cervix effacement.

27. The system of claim 23, the operations further comprising:
causing a change of the second visual indicator to another visual indicator.

28. The system of claim 27, wherein causing the change comprises at least one of a transformation or a variegation of the graphical object.

29. The system of claim 27, wherein the first visual indicator comprises a first color of the graphical object and the second visual indicator comprises a second color of the graphical object.

30. The system of claim 27, the operations further comprising causing display on the GUI of data representative of the clinical diagnostic simultaneously with the graphical object.

* * * * *